(12) United States Patent
Ishizuka et al.

(10) Patent No.: US 6,562,955 B2
(45) Date of Patent: May 13, 2003

(54) **OLIGONUCLEOTIDES FOR DETECTION OF *VIBRIO PARAHAEMOLYTICUS* AND DETECTION METHOD FOR *VIBRIO PARAHAEMOLYTICUS* USING THE SAME OLIGONUCLEOTIDES**

(75) Inventors: Tetsuya Ishizuka, Yokohama (JP); Takahiko Ishiguro, Yokohama (JP); Juichi Saitoh, Yamato (JP)

(73) Assignee: Tosoh Corporation, Yamaguchi-ken (JP)

( * ) Notice: Subject to any disclaimer, the term of this patent is extended or adjusted under 35 U.S.C. 154(b) by 0 days.

(21) Appl. No.: 09/808,358

(22) Filed: Mar. 15, 2001

(65) Prior Publication Data

US 2001/0031471 A1 Oct. 18, 2001

(30) Foreign Application Priority Data

| Mar. 17, 2000 | (JP) | 2000-081805 |
| Mar. 17, 2000 | (JP) | 2000-081806 |
| May 31, 2000 | (JP) | 2000-166503 |
| May 31, 2000 | (JP) | 2000-166504 |
| May 31, 2000 | (JP) | 2000-166505 |

(51) Int. Cl.[7] ............... C07H 21/02; C07H 21/04; C12P 19/34

(52) U.S. Cl. ............ 536/23.1; 536/24.1; 536/24.2; 536/24.3; 536/24.32; 536/24.33; 536/25.32; 435/91.1; 435/91.5; 435/91.51; 435/6

(58) Field of Search .............. 536/23.1, 24.1, 536/24.2, 24.33, 24.32, 24.3; 435/91.1, 91.2, 6, 91.5, 91.51

(56) References Cited

FOREIGN PATENT DOCUMENTS

JP          11318480       * 11/1999

OTHER PUBLICATIONS

GenEmbl Accession No. s67850 (sequence search results from SEQ ID Nos: 1–5 and 12–14).*

* cited by examiner

*Primary Examiner*—Kenneth R. Horlick
*Assistant Examiner*—Alexander H. Spiegler
(74) *Attorney, Agent, or Firm*—Jeffrey I. Auerbach; Liniak, Berenato & White

(57) ABSTRACT

An oligonucleotide for detection or amplification of a gene selected from the group consisting of *Vibrio parahaemolyticus* thermostable direct hemolysin-related hemolysin genes (trh1 and trh2) and *Vibrio parahaemolyticus* thermostable direct hemolysin gene (tdh2) or RNA derived therefrom is provided. Further, method for detecting trh1, trh2 or tdh2 using said oligonucleotide is provided.

9 Claims, 12 Drawing Sheets

Fig.7

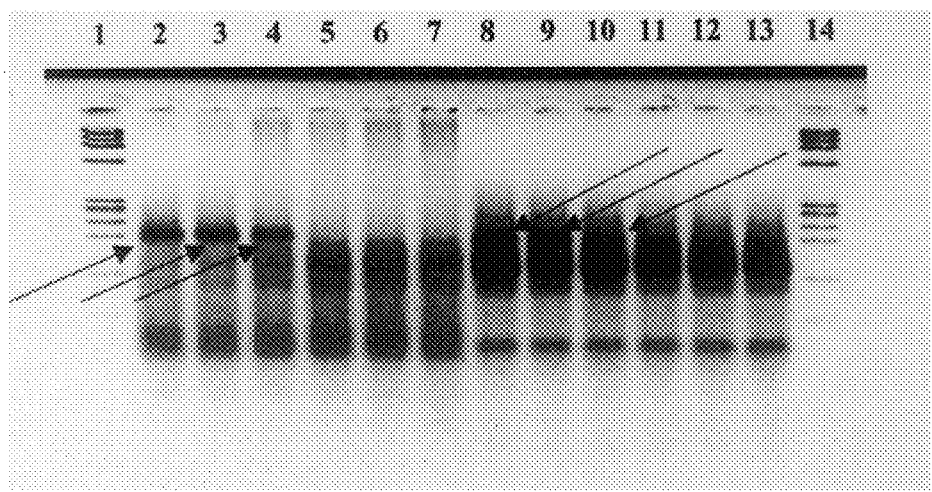

```
LANE   1st PRIMER   2nd PRIMER   CLEAVING PRIMER   TARGET RNA
2,3  ; SEQ ID 25    SEQ ID 28    SEQ ID 27         trh1 10^4 COPIES
4    ; SEQ ID 25    SEQ ID 28    SEQ ID 27         trh1 10^3 COPIES
5    ; SEQ ID 25    SEQ ID 28    SEQ ID 27         trh2 10^4 COPIES
6    ; SEQ ID 25    SEQ ID 28    SEQ ID 27         tdh2 10^4 COPIES
7    ; SEQ ID 25    SEQ ID 28    SEQ ID 27         Nega
8,9  ; SEQ ID 25    SEQ ID 29    SEQ ID 27         trh1 10^4 COPIES
10   ; SEQ ID 25    SEQ ID 29    SEQ ID 27         trh1 10^3 COPIES
11   ; SEQ ID 25    SEQ ID 29    SEQ ID 27         trh2 10^4 COPIES
12   ; SEQ ID 25    SEQ ID 29    SEQ ID 27         tdh2 10^4 COPIES
13   ; SEQ ID 25    SEQ ID 29    SEQ ID 27         Nega
1,14 ; DNA MW MARKER (φ×174/HaeIII DIGEST)
```

Fig.8

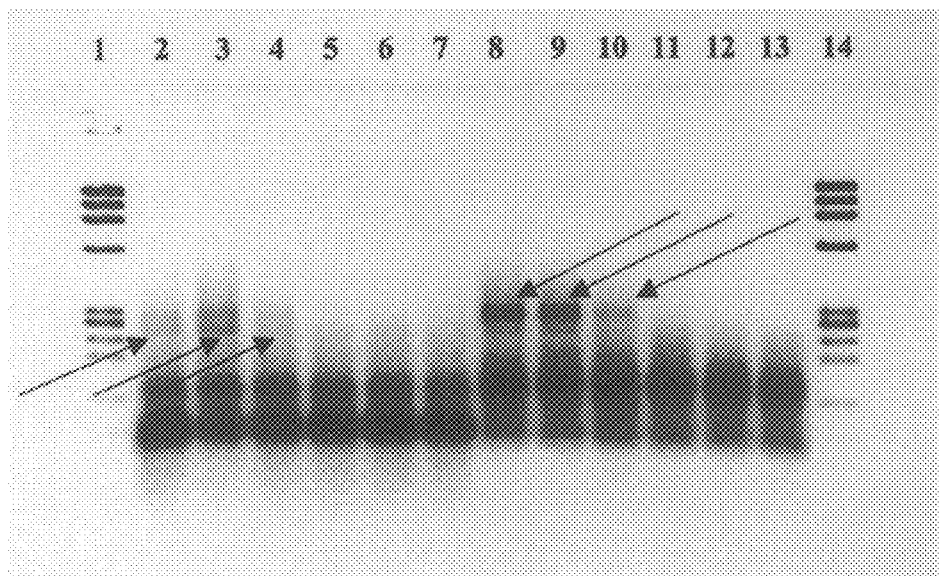

| LANE | 1st PRIMER | 2nd PRIMER | CLEAVING PRIMER | TARGET RNA | |
|---|---|---|---|---|---|
| 2,3 | ; SEQ ID 33 | SEQ ID 36 | SEQ ID 35 | trh2 | $10^4$ COPIES |
| 4 | ; SEQ ID 33 | SEQ ID 36 | SEQ ID 35 | trh2 | $10^3$ COPIES |
| 5 | ; SEQ ID 33 | SEQ ID 36 | SEQ ID 35 | trh1 | $10^4$ COPIES |
| 6 | ; SEQ ID 33 | SEQ ID 36 | SEQ ID 35 | tdh2 | $10^4$ COPIES |
| 7 | ; SEQ ID 33 | SEQ ID 36 | SEQ ID 35 | Nega | |
| 8,9 | ; SEQ ID 33 | SEQ ID 37 | SEQ ID 35 | trh2 | $10^4$ COPIES |
| 10 | ; SEQ ID 33 | SEQ ID 37 | SEQ ID 35 | trh2 | $10^3$ COPIES |
| 11 | ; SEQ ID 33 | SEQ ID 37 | SEQ ID 35 | trh1 | $10^4$ COPIES |
| 12 | ; SEQ ID 33 | SEQ ID 37 | SEQ ID 35 | tdh2 | $10^4$ COPIES |
| 13 | ; SEQ ID 33 | SEQ ID 37 | SEQ ID 35 | Nega | |
| 1,14 | ; DNA MW MARKER ($\phi \times 174$/HaeIII DIGEST) | | | | |

Fig. 9

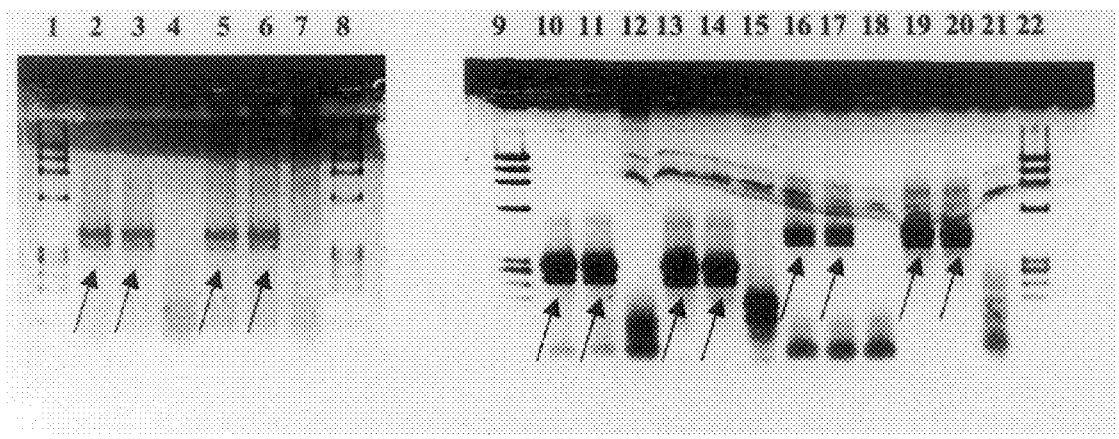

| LANE | 1st PRIMER | 2nd PRIMER | CLEAVING PRIMER | TARGET RNA |
|---|---|---|---|---|
| 2,3 | SEQ ID 39 | SEQ ID 43 | SEQ ID 44 | tdh $10^5$ COPIES |
| 4 | SEQ ID 39 | SEQ ID 43 | SEQ ID 44 | Nega |
| 5,6 | SEQ ID 39 | SEQ ID 45 | SEQ ID 44 | tdh $10^5$ COPIES |
| 7 | SEQ ID 39 | SEQ ID 45 | SEQ ID 44 | Nega |
| 10,11 | SEQ ID 39 | SEQ ID 46 | SEQ ID 47 | tdh $10^5$ COPIES |
| 12 | SEQ ID 39 | SEQ ID 46 | SEQ ID 47 | Nega |
| 13,14 | SEQ ID 39 | SEQ ID 48 | SEQ ID 47 | tdh $10^5$ COPIES |
| 15 | SEQ ID 39 | SEQ ID 48 | SEQ ID 47 | Nega |
| 16,17 | SEQ ID 42 | SEQ ID 46 | SEQ ID 47 | tdh $10^5$ COPIES |
| 18 | SEQ ID 42 | SEQ ID 46 | SEQ ID 47 | Nega |
| 19,20 | SEQ ID 42 | SEQ ID 48 | SEQ ID 47 | tdh $10^5$ COPIES |
| 21 | SEQ ID 42 | SEQ ID 48 | SEQ ID 47 | Nega |

1,8,9,22 ; DNA MW MARKER ($\phi$ ×174/HaeIII DIGEST)

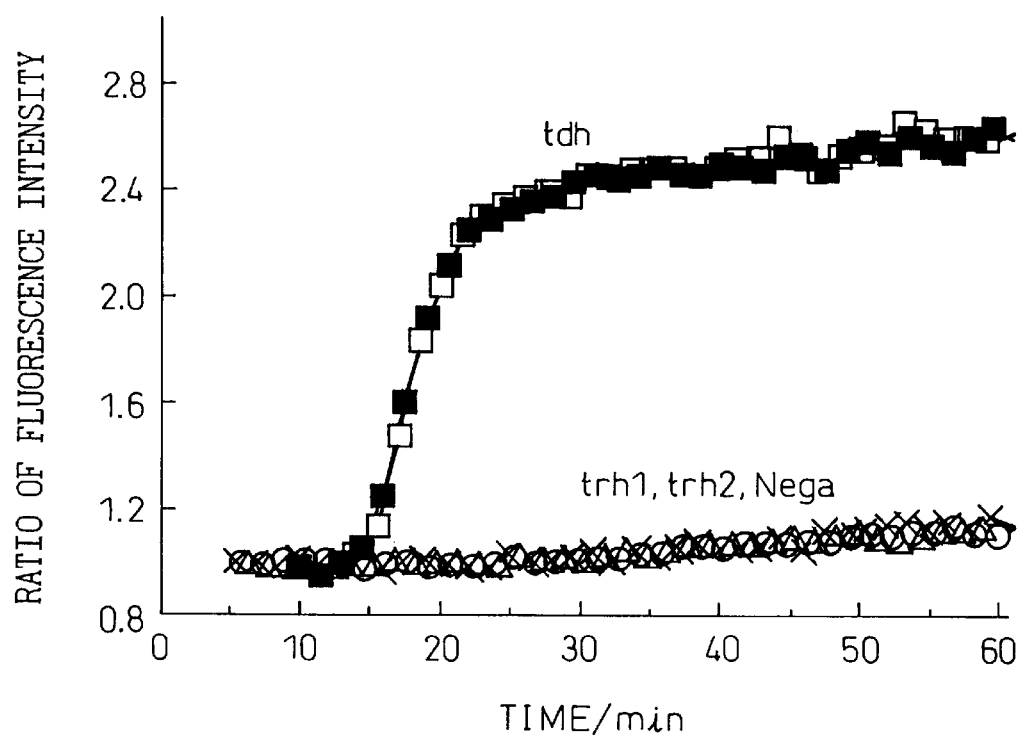

US 6,562,955 B2

OLIGONUCLEOTIDES FOR DETECTION OF VIBRIO PARAHAEMOLYTICUS AND DETECTION METHOD FOR VIBRIO PARAHAEMOLYTICUS USING THE SAME OLIGONUCLEOTIDES

FIELD OF THE INVENTION

The present invention relates to oligonucleotides for detection of *Vibrio parahaemolyticus* for clinical examination, public hygiene, food evaluation or food poisoning evaluation, and to detection methods for *Vibrio parahaemolyticus*.

PRIOR ART

*Vibrio parahaemolyticus* is known as a common infectious food poisoning bacteria. Over 95% of *Vibrio parahaemolyticus* isolated from gastroenteritis patients are Kanagawa phenomenon-positive bacteria exhibiting hemolytic activity in Wagatsuma agar medium, whereas 99% of these bacteria isolated from fish and water are Kanagawa phenomenon-negative bacteria. This had suggested a strong relationship between pathogenic *Vibrio parahaemolyticus* and the Kanagawa phenomenon, and later investigation revealed that the Kanagawa phenomenon is a phenomenon that occurs due to extracellular release of *Vibrio parahaemolyticus* thermostable direct hemolysin (TDH). As a result, TDH has come to notice as a pathogenic factor of *Vibrio parahaemolyticus*. More recently, certain pathogenic strains even among the Kanagawa phenomenon-negative strains have been confirmed to have a base sequence similar to that of TDH, and produce a hemolysin (TDH-related hemolysin: TRH) with partially common antigenicity.

Detection and identification of *Vibrio parahaemolyticus* has hitherto been complicated and time-consuming as it involves enrichment culturing and isolation culturing followed by determination of the Kanagawa phenomenon. Recently, detection and identification of *Vibrio parahaemolyticus* has been accomplished by the hybridization method using genetic probes specific to sequences in the TDH or TRH genes, but it has been difficult to obtain sufficient detection sensitivity for food evaluation and the like.

Thus, since identification of *Vibrio parahaemolyticus* requires complex procedures and prolonged periods, and a rapid detection of trace amounts of *Vibrio parahaemolyticus* in a sample was difficult to accomplish, a rapid and high sensitive detection method has been desired in fields such as food evaluation. In addition, in order to simplify the examination of interest, development of an automatic examination device has also been desired.

For highly sensitive detection, it is preferable to perform the detection after amplifying a specific sequence in the gene to be detected or identified, or in RNA derived from the gene (hereafter, these genes will collectively be referred to as "target nucleic acid").

When the target nucleic acid is DNA, Polymerase chain reaction (PCR) is known as an amplification method thereof. This method accomplishes amplification of a specific sequence in the target DNA by repetition of a cycle of heat denaturation, primer annealing and extension reaction in the presence of a pair of primers homologous and complementary to both ends of the specific sequence, as well as a thermostable DNA polymerase. However, the PCR method requires a complicated procedure involving repetition of rapidly increasing and decreasing the temperature, which prevents its automatization. In addition, amplification of a specific sequence by the PCR method requires oligonucleotides highly specific to the specific sequence, and oligonucleotides with high specificity to the target DNA are also required for highly sensitive detection and identification.

As amplification methods in cases where the target nucleic acid is RNA, there are known the NASBA method and 3SR method, whereby the specific sequence is amplified by the concerted action of reverse transcriptase and RNA polymerase. These methods involve a chain reaction, wherein a promoter sequence-containing primer for a specific sequence in the target RNA, reverse transcriptase, and Ribonuclease H are used to synthesize double-stranded DNA containing the promoter sequence, and this double-stranded DNA is used as a template for RNA polymerase-catalyzed synthesis of RNA containing the specific sequence, while the RNA in turn becomes a template for synthesis of double-stranded DNA containing the promoter sequence. The NASBA method and 3SR method can accomplish nucleic acid amplification at a constant temperature, and are therefore considered to be methods suitable for automation. However, since these amplification methods involve reaction at relatively low temperature (for example, 41° C.), the target RNA forms an intramolecular structure which inhibits binding of the primer, and may reduce the reaction efficiency. Consequently, a procedure of heat denaturation of the target RNA prior to the amplification reaction was required to break down the intramolecular structure of the target RNA, thereby to improve the primer binding efficiency. In addition, amplification of the specific sequence by the NASBA method requires an oligonucleotide with high specificity for the specific sequence, and an oligonucleotide with high specificity to the target RNA is also required for highly sensitive detection and identification. Even for RNA detection at low temperature, it is necessary to use an oligonucleotide that can bind to RNA that has formed the aforementioned intramolecular structure.

Therefore, the first object of the present invention is to provide an oligonucleotide that is useful for specific amplification of *Vibrio parahaemolyticus* thermostable direct hemolysin-related hemolysin genes (trh1 and trh2) or RNA derived from the genes, as well as for their highly sensitive detection and identification.

The second object of the present invention is to provide an oligonucleotide that is useful for specific amplification of *Vibrio parahaemolyticus* thermostable direct hemolysin gene (tdh2) or RNA derived from this gene, as well as for its highly sensitive detection and identification.

The third object of the present invention to provide a suitable combination of oligonucleotides useful for specific amplification of RNA derived from a *Vibrio parahaemolyticus* thermostable direct hemolysin-related hemolysin gene (trh1) at relatively low temperature (for example, 41° C.), as well as for highly sensitive detection and identification thereof.

The fourth object of the present invention to provide a suitable combination of oligonucleotides useful for specific amplification of RNA derived from a *Vibrio parahaemolyticus* thermostable direct hemolysin-related hemolysin gene (trh2) at relatively low temperature (for example, 41° C.), as well as for highly sensitive detection and identification thereof.

The fifth object of the present invention to provide a suitable combination of oligonucleotides useful for specific amplification of RNA derived from a *Vibrio parahaemolyticus* thermostable direct hemolysin gene (tdh2) at relatively low temperature (for example, 41° C.), as well as for highly sensitive detection and identification thereof.

DETAILED DESCRIPTION OF THE INVENTION

The invention of an oligonucleotide for detection or amplification of *Vibrio parahaemolyticus* thermostable direct hemolysin-related hemolysin genes (trh1 and trh2) or RNA derived from these genes, which oligonucleotide is capable of binding specifically to trh1 and trh2 or RNA derived therefrom, and comprises at least 10 contiguous bases of any of the sequences listed as SEQ. ID. Nos. 1 to 11, or an oligonucleotide complementary to said oligonucleotide, which has been accomplished to achieve the first object, relates to an oligonucleotide for detection or amplification of *Vibrio parahaemolyticus* thermostable direct hemolysin-related hemolysin genes (trh1 and trh2) or RNA derived from these genes, which oligonucleotide is capable of binding specifically to trh1 and trh2 or RNA derived therefrom, and comprises at least 10 contiguous bases of any of the sequences listed as SEQ. ID. Nos. 1 to 11, or an oligonucleotide complementary to said oligonucleotide.

The invention of an oligonucleotide for detection or amplification of a *Vibrio parahaemolyticus* thermostable direct hemolysin-related hemolysin gene (trh1) or RNA derived from said gene, which oligonucleotide is capable of binding specifically to trh1 or RNA derived therefrom, and comprises at least 10 contiguous bases of any of the sequences listed as SEQ. ID. Nos. 12 to 14, or an oligonucleotide complementary to said oligonucleotide, which has also been accomplished to achieve the aforementioned object, relates to an oligonucleotide for detection or amplification of a *Vibrio parahaemolyticus* thermostable direct hemolysin-related hemolysin gene (trh1) or RNA derived from said gene, which oligonucleotide is capable of binding specifically to trh1 or RNA derived therefrom, and comprises at least 10 contiguous bases of any of the sequences listed as SEQ. ID. Nos. 12 to 14, or an oligonucleotide complementary to said oligonucleotide.

The invention of an oligonucleotide for detection or amplification of a *Vibrio parahaemolyticus* thermostable direct hemolysin-related hemolysin gene (trh2) or RNA derived from said gene, which oligonucleotide is capable of binding specifically to trh2 or RNA derived therefrom, and comprises at least 10 contiguous bases of any of the sequences listed as SEQ. ID. Nos. 15 to 17, or an oligonucleotide complementary to said oligonucleotide, which has also been accomplished to achieve the aforementioned object, relates to an oligonucleotide for detection or amplification of a *Vibrio parahaemolyticus* thermostable direct hemolysin-related hemolysin gene (trh2) or RNA derived from said gene, which oligonucleotide is capable of binding specifically to trh2 or RNA derived therefrom, and comprises at least 10 contiguous bases of any of the sequences listed as SEQ. ID. Nos. 15 to 17, or an oligonucleotide complementary to said oligonucleotide.

The invention also concerns an oligonucleotide primer for a DNA extension reaction, comprising the above-described oligonucleotides. The invention also concerns an oligonucleotide probe a portion of which is modified or labeled with a detectable marker.

The invention of an oligonucleotide for detection or amplification of *Vibrio parahaemolyticus* thermostable direct hemolysin gene (tdh2) or RNA derived from said gene, which oligonucleotide is capable of binding specifically to tdh2 or RNA derived from said gene, and comprises at least 10 contiguous bases of any of the sequences listed as SEQ. ID. Nos. 18 to 24, or an oligonucleotide complementary to said oligonucleotide, which has been accomplished to achieve the second aforementioned object, relates to an oligonucleotide for detection or amplification of *Vibrio parahaemolyticus* thermostable direct hemolysin gene (tdh2) or RNA derived from said gene, which oligonucleotide is capable of binding specifically to tdh2 or RNA derived from said gene, and comprises at least 10 contiguous bases of any of the sequences listed as SEQ. ID. Nos. 18 to 24, or an oligonucleotide complementary to said oligonucleotide.

The invention also relates to an oligonucleotide primer for DNA extension reaction, comprising such an oligonucleotide as well as to an oligonucleotide probe comprising such an oligonucleotide, a portion of which is modified or labeled with a detectable marker.

The oligonucleotides of the invention, which have been accomplished to achieve the first and second aforementioned objects, respectively, are oligonucleotides that complementarily bind in a specific manner to intramolecular structure-free regions of the target RNA in the aforementioned RNA amplification, and they are capable of binding specifically to the target RNA without the heat denaturation described above. By providing oligonucleotides that bind to intramolecular structure-free regions of RNA derived from Vibrio parahaemolyticus trh1 and/or trh2 or tdh2 at a relatively low and constant temperature (35–50° C., and preferably 41° C.), the invention provides oligonucleotides for specific amplification and detection of trh1 and trh2, oligonucleotides for specific amplification and detection of trh1 alone, oligonucleotides for specific amplification and detection of trh2 alone, or oligonucleotides for specific amplification and detection of tdh2. More specifically, the invention encompasses oligonucleotide primers for amplification of target DNA by the PCR method, oligonucleotide primers for amplification of target RNA by the NASBA method, etc., and oligonucleotide probes for detection of target nucleic acid without or after amplification. By use of the oligonucleotides of the invention, a simple, rapid and highly sensitive detection method is provided for food evaluation and food poisoning evaluation.

SEQ. ID. Nos. 1 to 11 represent oligonucleotides for detection or amplification of trh1 and trh2, or RNA derived from these genes. "RNA derived from these genes" used herein includes RNA produced by using these genes as templates. The oligonucleotides may be oligonucleotides comprising at least 10 contiguous bases of any of the listed base sequences, or oligonucleotides complementary thereto.

SEQ. ID. Nos. 12 to 14 represent oligonucleotides for detection of trh1 or RNA derived from this gene, and they are useful for amplification or detection of trh1 as distinct from trh2. These oligonucleotides may be oligonucleotides comprising at least 10 contiguous bases of any of the listed base sequences, or oligonucleotides complementary thereto.

SEQ. ID. Nos. 15 to 17 represent oligonucleotides for detection of trh2 or RNA derived from this gene, and they are useful for amplification or detection of trh2 as distinct from trh1. These oligonucleotides may be oligonucleotides comprising at least 10 contiguous bases of any of the listed base sequences, or oligonucleotides complementary thereto.

SEQ. ID. Nos. 18 to 24 represent oligonucleotides for detection or amplification of tdh2, or RNA derived from this gene. "RNA derived from this genes" used herein includes RNA produced by using this gene as a template. The oligonucleotides may be oligonucleotides comprising at least 10 contiguous bases of any of the listed base sequences, or oligonucleotides complementary thereto.

One mode of each of the present inventions, to achieve the first or second aforementioned object, is an amplification primer comprising any of the aforementioned oligonucleotides. A nucleic acid amplification reaction carried out using an aforementioned oligonucleotide as the primer allows amplification of the target nucleic acid alone. The amplification method can be PCR method, NASBA method, 3SR method, etc., however, an isothermal nucleic acid amplification method such as NASBA or 3SR method is preferred. Detection of the amplification product by various methods allows detection of *Vibrio parahaemolyticus*. In this case, one of the aforementioned oligonucleotides other than the oligonucleotide used for amplification may be used as the probe, and fragments of the amplified specific sequence may be confirmed by electrophoresis or the like.

Another mode of each of the present invention to achieve the first or second aforementioned object is a probe which is any of the aforementioned oligonucleotides a portion of which is modified or labeled with a detectable marker. When detecting a target nucleic acid, the oligonucleotide labeled with the detectable marker may be hybridized with the single-stranded target nucleic acid, and the hybridized probe can be detected via the marker. The marker detection may be carried out by a method suitable for the particular marker and, for example, when using an intercalator fluorescent dye for labeling the oligonucleotide, a dye with the property of exhibiting increased fluorescent intensity by intercalation in the double-stranded nucleic acid comprising the target nucleic acid and the oligonucleotide probe may be used in order to allow easy detection of only the hybridized probe without removal of the probe that has not hybridized to the target nucleic acid. When using a common fluorescent dye as the marker, the marker may be detected after removal of the probe that has not hybridized to the target nucleic acid. For the detection, the target nucleic acid in the sample is preferably amplified to a detectable amount by a nucleic acid amplification method such as PCR, NASBA or 3SR method, among which isothermal nucleic acid amplification methods such as the NASBA and 3SR methods are most preferable. When incorporating the nucleotide-labeled probe in the reaction solution during the amplification, it is especially preferable to modify the probe by, for example, adding glycolic acid to the 3'-end so that the probe will not function as a nucleotide primer.

The inventions of a detection method:
(I) employing a RNA amplification process, which comprises the steps of: forming a cDNA with a RNA-dependent DNA polymerase using a specific sequence of a RNA derived from a *Vibrio parahaemolyticus* thermostable direct hemolysin-related hemolysin gene (trh1) present in a sample as a template, with a first primer having a sequence complementary to said specific sequence and a second primer having a sequence homologous to said specific sequence, wherein either the first or second primer has a sequence having the RNA polymerase promoter sequence added at its 5'-region, thereby producing a RNA-DNA double-strand; digesting the KNA of said RNA-DNA double-strand with Ribonuclease H to form a single-stranded DNA; and then forming a double-stranded DNA that includes a promoter sequence allowing transcription of said KNA sequence or a RNA comprising a sequence complementary to said RNA sequence with a DNA-dependent DNA polymerase using said single-stranded DNA as a template, said double-stranded DNA produces a RNA transcription product in the presence of a RNA polymerase, and said RNA transcription product is subsequently used as the template for the single-stranded DNA production with said RNA-dependent DNA polymerase; characterized in that the_ oligonucleotide of SEQ. ID. No.25 is used as the first primer and the oligonucleotide of SEQ. ID. No.26 is used as the second primer;

(II) employing a RNA amplification process, which comprises the steps of: forming a cDNA with a RNA-dependent DNA polymerase using a specific sequence of a RNA derived from a *Vibrio parahaemolyticus* thermostable direct hemolysin-related hemolysin gene (trh2) present in a sample as a template, with a first primer having a sequence complementary to said specific sequence and a second primer having a sequence homologous to said specific sequence, wherein either the first or second primer has a sequence_having the RNA polymerase promoter sequence added at its 5'-region, thereby producing a RNA-DNA double-strand; digesting the RNA of said RNA-DNA double-strand with Ribonuclease H to form a single-stranded DNA; and then forming a double-stranded DNA that includes a promoter sequence allowing transcription of said RNA sequence or a RNA comprising a sequence complementary to said RNA sequence with a DNA-dependent DNA polymerase using said single-stranded DNA as a template, said double-stranded DNA produces a_ RNA transcription product in the presence of a RNA polymerase, and said RNA transcription product is subsequently used as the template for the single-stranded DNA production with said RNA-dependent DNA polymerase; characterized in that the oligonucleotide of SEQ. ID. No.33 is used as the first primer and the oligonucleotide of SEQ. ID. No.34 is used as the second primer; or (III) employing a RNA amplification process, which comprises the steps of: forming a cDNA with a RNA-dependent DNA polymerase using a specific sequence of a RNA derived from a *Vibrio parahaemolyticus* thermostable direct hemolysin gene (tdh) present in a sample as a template, with a first primer having a sequence_ complementary to said specific sequence and a second primer having a sequence homologous to said specific sequence, wherein either the first or second primer has a sequence having the RNA polymerase promoter sequence added at its 5'-region, thereby producing a RNADNA double-strand; digesting the RNA of said RNA-DNA double-strand with Ribonuclease H to form a single-stranded DNA; and then forming a double-stranded DNA that includes a promoter sequence allowing transcription of said RNA sequence or a RNA comprising a sequence complementary to said RNA sequence with a DNA-dependent DNA polymerase using said single-stranded DNA as a template, said double-stranded DNA produces a RNA transcription product in the presence of a RNA polymerase, and said RNA_transcription product is subsequently used as the template for the single-stranded DNA production with said RNA-dependent DNA polymerase; characterized in that the oligonucleotide of SEQ. ID. No.39 is used as the first primer and the oligonucleotide of SEQ. ID. No.40 is used as the second primer, or the oligonucleotide of SEQ. ID. No.39 is used as the first primer and the oligonucleotide of SEQ. ID. No.41 is used as the second primer, or the oligonucleotide of SEQ. ID. No.42 is used as the first primer and the oligonucleotide of SEQ. ID. No.41 is used as the second primer; which have been accomplished to achieve the third, fourth and fifth aforementioned objects, respectively, relate to a detection method employing a RNA amplification process, which comprises the steps of: forming a cDNA with a RNA-dependent DNA polymerase using a specific sequence of a RNA derived from trh1, trh2 or tdh2 present in a sample as a template, with a first primer having a sequence complementary to said specific sequence and a second primer having a sequence homologous to said specific sequence, wherein either the first or second primer has a sequence having the RNA polymerase promoter sequence added at its 5'-region, thereby producing a RNA-DNA double-strand; digesting the RNA of said RNA-DNA double-strand with Ribonuclease H to form a single-stranded DNA; and then forming a double-stranded DNA that includes a promoter sequence allowing transcription of said RNA sequence or a RNA comprising a sequence complementary to said RNA sequence with a DNA-dependent DNA polymerase using said single-stranded DNA as a template, said double-stranded DNA produces a RNA transcription product in the presence of a RNA polymerase, and said RNA transcription product is subsequently used as the template for the single-stranded DNA production with said RNA-dependent DNA polymerase; characterized in that, as for trh1, the oligonucleotide of SEQ. ID. No.25 is used as the first primer and the oligonucleotide of SEQ. ID. No.26 is used as the second primer, as for trh2, the oligonucleotide of SEQ. ID. No.33,is used as the first primer and the oligonucleotide of SEQ. ID. No.34 is used as the second primer, as for tdh2, the oligonucleotide of SEQ. ID. No.39 is used as the first primer and the oligonucleotide of SEQ. ID. No.40 is used as the second primer, or the oligonucleotide of SEQ. ID. No.39 is used as the first primer and the oligonucleotide of SEQ. ID. No.41 is used as the second primer, or the oligonucleotide of SEQ. ID. No.42 is used as the first primer and the oligonucleotide of SEQ. ID. No.41 is used as the second primer.

The invention an embodiment of such method (I), characterized in that said first primer is an oligonucleotide comprising at least 10 contiguous bases of the sequence of SEQ. ID. No.25, has been accomplished to achieve the third aforementioned object. The invention also relates to the embodiment of such method (I) characterized in that the second primer is an oligonucleotide comprising at least 10 contiguous bases of the sequence of SEQ. ID. No.26. The invention of a detection method for a *Vibrio parahaemolyticus* thermostable direct hemolysin-related hemolysin gene, which comprises the steps of:_conducting the RNA amplification process in the presence of an oligonucleotide probe labeled with an intercalator fluorescent dye, wherein the sequence of said probe is complementary to at least a portion of said RNA transcription product, and complementary binding of said probe to said RNA transcription product results in a change of the fluorescent property relative to that of a situation where a complex formation is absent; and then measuring the fluorescence intensity of the reaction solution_relates to an embodiment of such method (I) and is a detection method for a *Vibrio parahaemolyticus* thermostable direct hemolysin-related hemolysin gene, which comprises the steps of: conducting said RNA amplification process in the presence of an oligonucleotide probe labeled with an intercalator fluorescent dye, wherein the sequence of said probe is complementary to at least a portion of said RNA transcription product, and complementary binding of said probe to said RNA transcription product results in a change of the fluorescent property relative to that of a situation where a complex formation is absent; and then measuring the fluorescence intensity of the reaction solution.

The invention also concerns an embodiment of the detection method (II), characterized in that said first primer is an oligonucleotide comprising at least 10 contiguous bases of the sequence of SEQ. ID. No.33., has been accomplished to achieve the fourth aforementioned object. The invention also relates to the embodiment of such detection method (II) characterized in that the second primer is an oligonucleotide comprising at least 10 contiguous bases of the sequence of SEQ. ID. No.34. The invention also relates to the embodiment of such detection method (II) which comprises the steps of: conducting said RNA amplification process in the presence of an oligonucleotide probe labeled with an intercalator fluorescent dye, wherein the sequence of said probe is complementary to at least a portion of said RNA transcription product, and complementary binding of said probe to said RNA transcription product results in a change of the fluorescent property relative to that of a situation where a complex formation is absent; and then measuring the fluorescence intensity of the reaction solution.

The embodiment of such detection method (III) which has been accomplished to achieve the fifth aforementioned object, is characterized in that the first primer is an oligonucleotide comprising at least 10 contiguous bases of the sequence of SEQ. ID. No.39 or SEQ. ID. No.42. The invention also relates to an embodiment of such detection method (III) characterized in that the second primer is an oligonucleotide comprising at least 10 contiguous bases of the sequence of SEQ. ID. No.40 or SEQ. ID. No.41. The invention also relates to an embodiment of such detection method (III) which comprises the steps of: conducting said KNA amplification process in the presence of an oligonucleotide probe labeled with an intercalator fluorescent dye, wherein the sequence of said probe is complementary to at least a portion of said RNA transcription product, and complementary binding of said probe to said RNA transcription product results in a change of the fluorescent property relative to that of a situation where a complex formation is absent; and then measuring the fluorescence intensity of the reaction solution.

By providing a combination of oligonucleotides for detection of RNA derived from *Vibrio parahaemolyticus* trh1, trh2 or tdh2, at a relatively low and constant temperature (35–50° C., and preferably 41° C.), i.e., providing a combination of an oligonucleotide primer for amplification of trh1-derived RNA and an oligonucleotide probe for detection thereof, the inventions which has been accomplished to achieve the third, fourth and fifth objects, respectively, provide a detection method and detection kit for simple, rapid and highly sensitive detection of the *Vibrio parahaemolyticus* thermostable direct hemolysin-related hemolysin gene (trh1 or trh2) or *Vibrio parahaemolyticus* thermostable direct hemolysin gene (tdh2), for food evaluation and food poisoning evaluation.

According to one mode of each of the present inventions to achieve the third, fourth or fifth aforementioned object, the first primer (a sequence complementary to the 3'-end region of a specific sequence of the target RNA) complementarily binds to a specific sequence of RNA derived from the *Vibrio parahaemolyticus* thermostable direct hemolysin-related hemolysin gene (trh1 or trh2) or the *Vibrio parahaemolyticus* thermostable direct hemolysin gene (tdh2) in a sample as the template, and cDNA is produced by extension reaction with RNA-dependent DNA polymerase to form a RNA-DNA double-strand, after which the RNA of the RNA-DNA double-strand is digested with Ribonuclease H to produce a single-stranded DNA. Next, a second primer (a sequence homologous to the 5'-end region of the target RNA, and includes the RNA polymerase promoter sequence added at its 5'-end) complementarily binds to the single-stranded DNA, to produce a double-stranded DNA having a promoter sequence allowing transcription of RNA comprising a sequence homologous to the target RNA sequence, using DNA-dependent DNA polymerase. The double-stranded DNA is then used for amplification of the RNA transcription product comprising the sequence homologous to the target RNA sequence in the presence of RNA polymerase. The present invention is characterized in that, as for trh1, the oligonucleotide of SEQ. ID. No.25 is used as the first primer and the oligonucleotide of SEQ. ID. No.26 is used as the second primer, as for trh2, the oligonucleotide of SEQ. ID. No.33 is used as the first primer and the oligonucleotide of SEQ. ID. No.34 is used as the second primer, as for tdh2, the oligonucleotide of SEQ. ID. No.39 is used as the first primer and the oligonucleotide of SEQ. ID. No.40 is used as the second primer, or the oligonucleotide of SEQ. ID. No.39 is used as the first primer and the oligonucleotide of SEQ. ID. No.41 is used as the second primer, or the oligonucleotide of SEQ. ID. No.42 is used as the first primer and the oligonucleotide of SEQ. ID. No.41 is used as the second primer. For tdh2, it is particularly preferable to use the oligonucleotide of SEQ. ID. No.42 as the first primer and the oligonucleotide of SEQ. ID. No.41 as the second primer.

The first and second primers may be the full-length base sequences of SEQ. ID. Nos.25, 33, 39, 42 and SEQ. ID. Nos.26, 34, 40, 41, respectively, however, combinations of oligonucleotides comprising at least 10 contiguous bases of these sequences may also be used.

According to this mode of each of the present inventions, to achieve the third, fourth or fifth aforementioned object, the target RNA must be cleaved at the 5'-end of the specific sequence. The method of cleaving the target RNA is preferably a method in which an oligonucleotide (cleaving oligonucleotide) with a sequence complementary to a region overlapping and adjacent to the 5'-end of the specific sequence is added, thereby cleaving the target RNA with Ribonuclease H or the like. The 3'-end of the cleaving oligonucleotide is preferably treated by amination, for example, to prevent it from functioning as an oligonucleotide primer.

According to this mode of each of the present inventions, to achieve the third, fourth or fifth aforementioned objects, the amplification process is preferably carried out in the presence of an oligonucleotide probe labeled with an intercalator fluorescent dye having a sequence complementary to at least a portion of the RNA transcription product. Complementary binding of the probe to the RNA transcription product results in a change of the fluorescent property compared to a situation where the complex formation is absent, so that the fluorescence intensity of the reaction solution may be measured. When a labeled oligonucleotide probe is incorporated during the amplification process, it is particularly preferable to modify the probe by, for example, addition of glycolic acid to the 3'-end, to prevent it from functioning as a primer in the extension reaction.

For trh1, the oligonucleotide probe used may be an oligonucleotide comprising at least 10 contiguous bases of the sequences listed as SEQ. ID. Nos.30 to 32.

For trh2, the oligonucleotide probe used may be an oligonucleotide comprising at least 10 contiguous bases of the sequences listed as SEQ. ID. No.38.

For tdh2, the oligonucleotide probe used may be an oligonucleotide comprising at least 10 contiguous bases of SEQ. ID. No.39, when a combination of oligonucleotides comprising at least 10 contiguous bases of SEQ. ID. No.41 and SEQ. ID. No.42 are used for the RNA amplification process.

According to another mode of each of the present inventions, to achieve the third, fourth or fifth aforementioned object, the first primer (a sequence complementary to the target RNA, and including the RNA polymerase promoter sequence added at the 5'-region) complementarily binds to a specific sequence of RNA derived from trh1, trh2 or tdh2 in a sample as the template, and cDNA is produced by extension reaction with RNA-dependent DNA polymerase to form a RNA-DNA double-strand, after which the RNA of the RNA-DNA double-strand is digested with Ribonuclease H to produce single-stranded DNA. Next, the second primer (a sequence homologous to the target RNA) complementarily binds to the single-stranded DNA, to produce double-stranded DNA having a promoter allowing transcription of RNA comprising a sequence complementary to the target RNA sequence, using DNA-dependent DNA polymerase. The double-stranded DNA is then used to produce a RNA transcription product comprising a sequence complementary to the target RNA, in the presence of RNA polymerase. The second primer complementarily binds to this RNA transcription product (the sequence complementary to the target RNA), and cDNA is produced with RNA-dependent DNA polymerase to form a double-strand of RNA-DNA. Next, the RNA of the RNA-DNA double-strand is digested with Ribonuclease H to produce single-stranded DNA, and the first primer complementarily binds to this single-stranded DNA to produce double-stranded DNA having a promoter allowing transcription of RNA comprising a sequence complementary to the target RNA sequence, using DNA-dependent DNA polymerase. The double-stranded DNA is then used for amplification of the RNA transcription product comprising a sequence complementary to the target RNA sequence in the presence of RNA polymerase. The present invention is characterized in that, as for trh1, the oligonucleotide of SEQ. ID. No.25 is used as the first primer and the oligonucleotide of SEQ. ID. No.26 is used as the second primer, as for trh2, the oligonucleotide of SEQ. ID. No.33 is used as the first primer and the oligonucleotide of SEQ. ID. No.34 is used as the second primer, as for tdh2, the oligonucleotide of SEQ. ID. No.39 is used as the first primer and the oligonucleotide of SEQ. ID. No.40 is used as the second primer, or the oligonucleotide of SEQ. ID. No.39 is used as the first primer and the oligonucleotide of SEQ. ID. No.41 is used as the second primer, or the oligonucleotide of SEQ. ID. No.42 is used as the first primer and the oligonucleotide of SEQ. ID. No.41 is used as the second primer. For tdh2, it is particularly preferable to use the oligonucleotide of SEQ. ID. No.42 as the first primer and the oligonucleotide of SEQ. ID. No.41 as the second primer.

The first and second primers may be the full-length base sequences of SEQ. ID. Nos.25, 33, 39, 42 and SEQ. ID. Nos.26, 34, 40, 41, respectively, however, combinations of oligonucleotides comprising at least 10 contiguous bases of these sequences may also be used.

According to this mode of each of the present inventions, to achieve the third, fourth or fifth aforementioned object, the amplification process is preferably carried out in the presence of an oligonucleotide probe labeled with an intercalator fluorescent dye having a sequence complementary to at least a portion of the RNA transcription product. Complementary binding of the probe to the RNA transcription product produces a change in the fluorescent property relative to that of a situation where the complex formation is absent, so that the fluorescence intensity of the reaction solution may be measured. When a labeled oligonucleotide probe is incorporated during the amplification process, it is particularly preferable to modify the probe by, for example, addition of glycolic acid to the 3'-end, to prevent it from functioning as a primer in the extension reaction.

For trh1, the oligonucleotide probe used may be a sequence complementary to an oligonucleotide comprising at least 10 contiguous bases of the sequences listed as SEQ. ID. Nos.30 to 32.

For trh2, the oligonucleotide probe used may be a sequence complementary to an oligonucleotide comprising at least 10 contiguous bases of the sequences listed as SEQ. ID. No.38.

For tdh2, the oligonucleotide probe used may be a sequence complementary to an oligonucleotide comprising at least 10 contiguous bases of SEQ. ID. No.39, when a combination of oligonucleotides comprising at least 10 contiguous bases of SEQ. ID. No.41 and SEQ. ID. No.42 are used for the RNA amplification process.

BRIEF DESCRIPTION OF THE DRAWINGS

FIG. 7 illustrates the results of the RNA amplification reaction of Example 7, carried out with different primer combinations at an initial RNA amount of $10^4$ copies/30 $\mu$l and $10^3$ copies/30 $\mu$l. "Nega" represents a sample using the diluent alone instead of a RNA sample.

FIG. 8 illustrates the results of the RNA amplification reaction of Example 8, carried out with different primer combinations at an initial RNA amount of $10^4$ copies/30 $\mu$l and $10^3$ copies/30 $\mu$l. "Nega" represents a sample using the diluent alone instead of a RNA sample.

FIG. 9 illustrates the results of the RNA amplification reaction of Example 9, carried out with different primer combinations at an initial RNA amount of $10^5$ copies/30 $\mu$l. "Nega" represents a sample using the diluent alone instead of a RNA sample.

FIG. 12 illustrates a graph of the reaction time and fluorescence rate increase obtained by using tdh2-RNA, trh1-RNA and trh2-RNA as the target RNA in Example 11. "Nega" represents the results using the diluent alone instead of a RNA sample.

EXAMPLES

Figure 1:
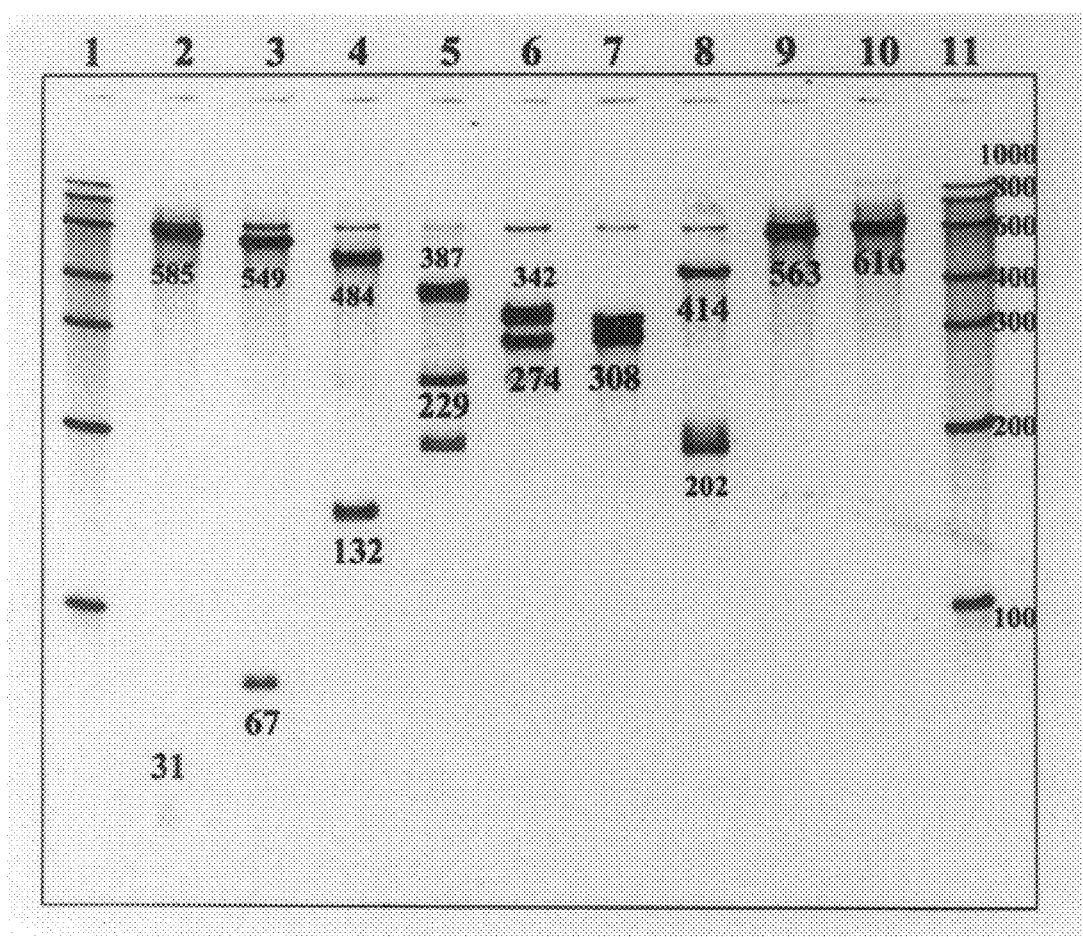
FIG. 1 illustrates an electrophoresis image of 6% PAGE for a sample after performing a binding test to trh1-RNA at 41° C., using oligonucleotides designed for an intramolecular structure-free region of trh1-RNA. In the image, lanes 1 and 11 are the RNA marker (0.1 to 1.0 K), lanes 2 to 9 relate to oligonucleotide solutions of SEQ. ID. No.1, 2, 3, 4, 12, 5, 13 and 14, respectively, and lane 10 is a standard sample of trh1-RNA (616 mer).

The present invention will now be explained in greater detail by way of examples, with the understanding that the invention is not limited by these examples.

1. Oligonucleotide Which Complementarily Binds to RNA Derived from trh1 and/or trh2

Example 1

Specific binding of the oligonucleotides of the invention to trh1-RNA at 41° C. was examined. The trh1-RNA is a synthesized and purified RNA obtained by in vitro transcription using double-stranded DNA containing the trh1 base sequence as the template.

First, a sample of a standard RNA (616 mer) comprising base Nos. 1 to 610 of *Vibrio parahaemolyticus* trh1-RNA (the RNA base sequence numbering is in accordance with Nishibuchi et al. "Appl. Environ. Microbiol., 1992, 58, pp.2449–2457") was quantified by ultraviolet absorption at 260 nm, and then diluted with a RNA diluent (10 mM Tris-HCl (pH 8.0), 0.1 mM EDTA, 0.5 U/$\mu$l RNase Inhibitor) to $3.0 \times 10^{-12}$ mol/$\mu$l.

Next, 14.0 $\mu$l of a reaction solution with the following composition was dispensed into a 0.5 ml volume PCR tube (GeneAmp Thin-Walled Reaction®; Perkin-Elmer Co., Ltd.).

Composition of Reaction Solution 20.0 mM Tris-HCl buffer (pH 7.5)
20.0 mM potassium chloride 10.0 mM magnesium chloride 0.1 mM DTT 0.1 mM EDTA 1.3 µM of oligonucleotide primer solution 1.0×10⁻¹² mol standard trh1-RNA sample Distilled water for volume adjustment As the oligonucleotide primer solutions, the oligonucleotide solution of SEQ. ID. No.1, the oligonucleotide solution of SEQ. ID. No.2, the oligonucleotide solution of SEQ. ID. No.3, the oligonucleotide solution of SEQ. ID. No.4, the oligonucleotide solution of SEQ. ID. No.12, the oligonucleotide solution of SEQ. ID. No.13, the oligonucleotide solution of SEQ. ID. No.5 and the oligonucleotide solution of SEQ. ID. No.14 were used. The oligonucleotide of SEQ. ID. No.1 is complementary to the 20 mer sequence from Nos. 31 to 50 of trh1-RNA, the oligonucleotide of SEQ. ID. No.2 is complementary to the 20 mer sequence from Nos. 67 to 86 of trh1-RNA, the oligonucleotide of SEQ. ID. No.3 is complementary to the 20 mer sequence from Nos. 132 to 151 of trh1-RNA, the oligonucleotide of SEQ. ID. No. 4 is complementary to the 20 mer sequence from Nos. 229 to 248 of trh1-RNA, the oligonucleotide of SEQ. ID. No.12 is complementary to the 20 mer sequence from Nos. 274 to 293 of trh1-RNA, the oligonucleotide of SEQ. ID. No.5 is complementary to the 20 mer sequence from Nos. 308 to 327 of trh1-RNA, the oligonucleotide of SEQ. ID. No.13 is complementary to the 20 mer sequence from Nos. 414 to 433 of trh1-RNA, and the oligonucleotide of SEQ. ID. No.14 is complementary to the 20 mer sequence from Nos. 563 to 582 of trh1-RNA.

The reaction solution was then incubated at 41° C. for 5 minutes, 0.1 U of RNase H (Takara Shuzo Co., Ltd.) was added (RNase H is an enzyme that cleaves the RNA of DNA/RNA double strands), and the PCR tube was incubated at 41° C. for 15 minutes.

Polyacrylamide gel (acrylamide concentration: 6%, urea: 7 M) electrophoresis was conducted to confirm the cleaved fragments after the reaction. Dyeing after electrophoresis was carried out with SYBR Green II (Takara Shuzo Co., Ltd.). Upon binding of the oligonucleotide to the specific site of the target RNA, the RNA of the DNA/RNA double strands is cleaved by RNase H and characteristic bands are observed.

The electrophoresis results are shown in FIG. 1 (FIG. 1 is a photograph showing the state of the oligonucleotides (black and white inverted)). The sizes of the newly appeared characteristic bands were as shown in FIG. 1. For example, in the experiment using the oligonucleotide of SEQ. ID. No.1, the sizes of the bands obtained by cleaving from the 31st base from the 5'-end of trh1-RNA, i.e. a 31 mer and a 585 mer, are shown. Since characteristic bands were confirmed in the experiments using all of the aforementioned oligonucleotides in this manner, it was demonstrated that all of these oligonucleotides bind strongly to *Vibrio parahaemolyticus* trh1-RNA at 41° C.

Example 2

Specific binding of the oligonucleotides of the invention to trh2-RNA at 41° C. was examined. The trh2-RNA is a synthesized and purified RNA obtained by in vitro transcription using double-stranded DNA containing the trh2 base sequence as the template.

First, a sample of a standard RNA (616 mer) comprising base Nos. 1 to 610 of *Vibrio parahaemolyticus* trh2-RNA (the RNA base sequence numbering is in accordance with Nishibuchi et al. "Appl. Environ. Microbiol., 1992, 58, pp.2449–2457") was quantified by ultraviolet absorption at 260 nm, and then diluted with a RNA diluent (10 mM Tris-HCl (pH 8.0), 0.1 mM EDTA, 0.5 U/µl RNase Inhibitor) to 3.0×10⁻¹² mol/µl.

Next, 14.0 µl of a reaction solution with the following composition was dispensed into a 0.5 ml volume PCR tube (GeneAmp Thin-Walled Reaction Tubes®; Perkin-Elmer Co., Ltd.).

Composition of Reaction Solution 20.0 mM Tris-HCl buffer (pH 7.5)

20.0 mM potassium chloride 10.0 mM magnesium chloride 0.1 MM DTT 0.1 mM EDTA 1.3 µM of oligonucleotide primer solution 1.0×10⁻¹² mol standard trh2-RNA sample Distilled water for volume adjustment As the oligonucleotide primer solutions, the oligonucleotide solution of SEQ. ID. No.1, the oligonucleotide solution of SEQ. ID. No.2, the oligonucleotide solution of SEQ. ID. No.3, the oligonucleotide solution of SEQ. ID. No.12, the oligonucleotide solution of SEQ. ID. No.5, the oligonucleotide solution of SEQ. ID. No.13, the oligonucleotide solution of SEQ. ID. No.14 and the oligonucleotide solution of SEQ. ID. No.8 were used. The oligonucleotide of SEQ. ID. No. 1 is complementary to the 20 mer sequence from Nos. 31 to 50 of trh1-RNA, the oligonucleotide of SEQ. ID. No.2 is complementary to the 20 mer sequence from Nos. 67 to 86 of trh1-RNA, the oligonucleotide of SEQ. ID. No.3 is complementary to the 20 mer sequence from Nos. 132 to 151 of trh1-RNA, the oligonucleotide of SEQ. ID. No.12 is complementary to the 20 mer sequence from Nos. 274 to 293 of trh1-RNA, the oligonucleotide of SEQ. ID. No.5 is complementary to the 20 mer sequence from Nos. 308 to 327 of trh1-RNA, the oligonucleotide of SEQ. ID. No.13 is complementary to the 20 mer sequence from Nos. 414 to 433 of trh1-RNA, the oligonucleotide of SEQ. ID. No.14 is complementary to the 20 mer sequence from Nos. 563 to 582 of trh1-RNA, and the oligonucleotide of SEQ. ID. No.8 is complementary to the 20 mer sequence from Nos. 259 to 278 of trh2-RNA.

The reaction solution was then incubated at 41° C. for 5 minutes, 0.1 U of RNase H (Takara Shuzo Co., Ltd.) was added (RNase H is an enzyme that cleaves the RNA of DNA/RNA double strands), and the PCR tube was incubated at 41° C. for 15 minutes.

Polyacrylamide gel (acrylamide concentration: 6%, urea: 7 M) electrophoresis was conducted to confirm the cleaved fragments after the reaction. Dyeing after electrophoresis was carried out with SYBR Green II (Takara Shuzo Co., Ltd.). Upon binding of the oligonucleotide to the specific site of the target RNA, the RNA of the DNA/RNA double strands is cleaved by RNase H and characteristic bands are observed.

Figure 2:
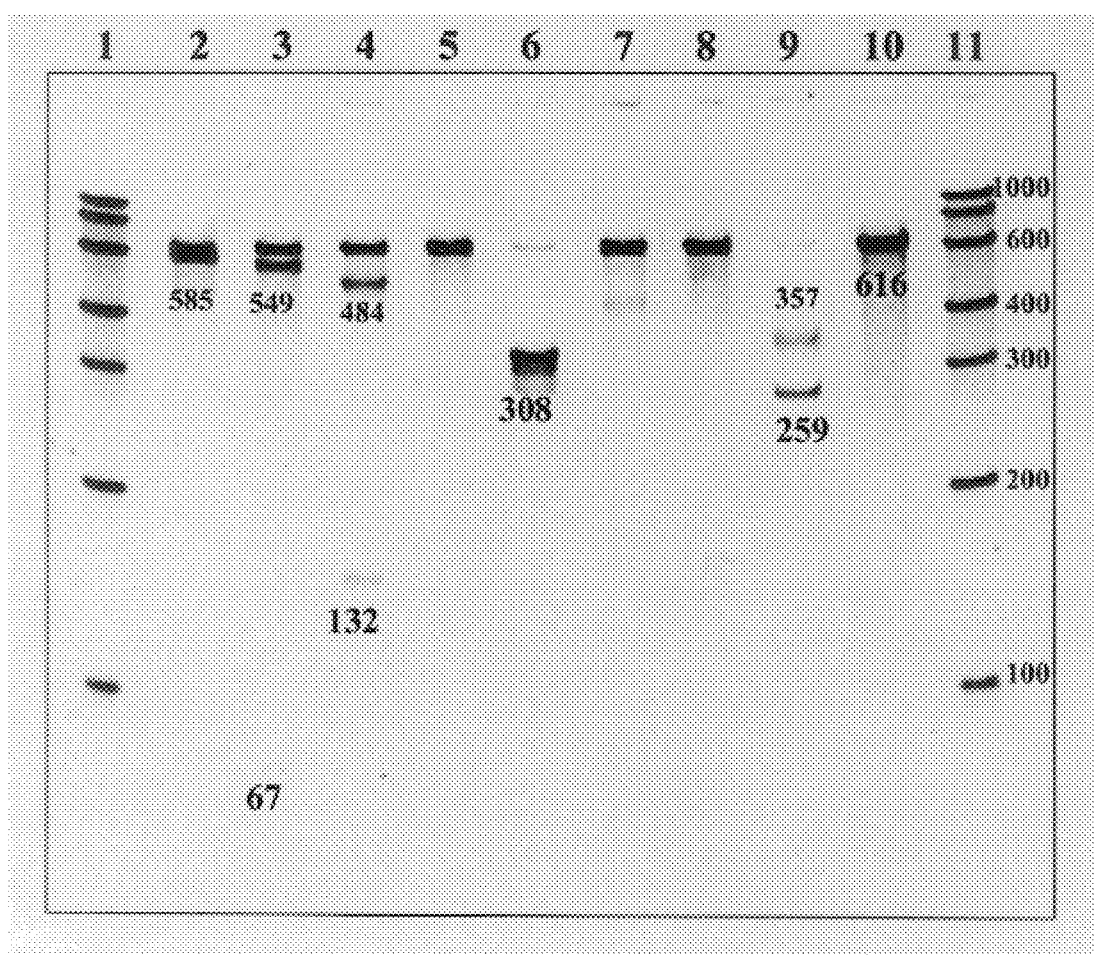
FIG. 2 illustrates an electrophoresis image of 6% PAGE for a sample after performing a binding test to trh2-RNA at 41° C., using oligonucleotides designed for an intramolecular structure-free region of trh1-RNA. In the image, lanes 1 and 11 are the RNA marker (0.1 to 1.0 K), lanes 2 to 9 relate to oligonucleotide solutions of SEQ. ID. No.1, 2, 3, 12, 5, 13, 14 and 8 respectively, and lane 10 is a standard sample of trh2-RNA (616 mer).

The electrophoresis results are shown in FIG. 2 (FIG. 2 is a photograph showing the state of the oligonucleotides (black and white inverted)). The sizes of the newly appeared characteristic bands were as shown in FIG. 2. For example, in the experiment using the oligonucleotide of SEQ. ID. No.2, the sizes of the bands obtained by cleaving from the 67th base from the 5'-end of trh1-RNA, i.e. a 67 mer and a 549 mer, are shown.

Since characteristic bands were confirmed in the experiments using the oligonucleotides of SEQ. ID. No.1, SEQ.

ID. No.2, SEQ. ID. No.3 and SEQ. ID. No.5 in this manner, it was demonstrated that the oligonucleotides with these sequences bind strongly to *Vibrio parahaemolyticus* trh2-RNA at 41° C. On the other hand, the oligonucleotides of SEQ. ID. No.12, SEQ. ID. No.13 and SEQ. ID. No.14 did not bind to the trh2-RNA. Also, the oligonucleotide of SEQ. ID. No.8 was used as a control sequence that binds strongly to trh2-RNA at 41° C. In light of the results of Example 1, it was demonstrated that the oligonucleotides of SEQ. ID. No.1, SEQ. ID. No.2, SEQ. ID. No.3 and SEQ. ID. No.5 bind strongly to both trh1-RNA and trh2-RNA at 41° C. On the other hand, it was demonstrated that the oligonucleotides of SEQ. ID. No.12, SEQ. ID. No.13 and SEQ. ID. No.14 bind strongly only to trh1-RNA at 41° C.

Example 3

Specific binding of the oligonucleotides of the invention to trh2-RNA at 41° C. was examined.

First, a sample of a standard RNA (616 mer) comprising base Nos. 1 to 610 of trh2-RNA was quantified by ultraviolet absorption at 260 nm, and then diluted with a RNA diluent (10 mM Tris-HCl (pH 8.0), 0.1 mM EDTA, 0.5 U/µl RNase Inhibitor) to $3.0 \times 10^{-12}$ mol/µl.

Next, 14.0 µl of a reaction solution with the following composition was dispensed into a 0.5 ml volume PCR tube (GeneAmp Thin-Walled Reaction Tubes®; Perkin-Elmer Co., Ltd.).

Composition of Reaction Solution 20.0 mM Tris-HCl buffer (pH 7.5)
20.0 mM potassium chloride
10.0 mM magnesium chloride
0.1 mM DTT
0.1 mM EDTA
1.3 µM of oligonucleotide primer solution
$1.0 \times 10^{-12}$ mol standard trh2-RNA sample
Distilled water for volume adjustment As the oligonucleotide primer solutions, the oligonucleotide solution of SEQ. ID. No.6, the oligonucleotide solution of SEQ. ID. No.15, the oligonucleotide solution of SEQ. ID. No.7, the oligonucleotide solution of SEQ. ID. No.8, the oligonucleotide solution of SEQ. ID. No.16, the oligonucleotide solution of SEQ. ID. No.17, the oligonucleotide solution of SEQ. ID. No.9, the oligonucleotide solution of SEQ. ID. No.10 and the oligonucleotide solution of SEQ. ID. No.11 were used. The oligonucleotide of SEQ. ID. No.6 is complementary to the 20 mer sequence from Nos. 55 to 74 of trh2-RNA, the oligonucleotide of SEQ. ID. No.15 is complementary to the 20 mer sequence from Nos. 84 to 103 of trh2-RNA, the oligonucleotide of SEQ. ID. No.7 is complementary to the 20 mer sequence from Nos. 131 to 150 of trh2-RNA, the oligonucleotide of SEQ. ID. No.8 is complementary to the 20 mer sequence from Nos. 259 to 278 of trh2-RNA, the oligonucleotide of SEQ. ID. No.16 is complementary to the 20 mer sequence from Nos. 322 to 341 of trh2-RNA, the oligonucleotide of SEQ. ID. No.17 is complementary to the 20 mer sequence from Nos. 380 to 399 of trh2-RNA, the oligonucleotide of SEQ. ID. No.9 is complementary to the 20 mer sequence from Nos. 407 to 426 of trh2-RNA, the oligonucleotide of SEQ. ID. No.10 is complementary to the 20 mer sequence from Nos. 456 to 475 of trh2-RNA, and the oligonucleotide of SEQ. ID. No.11 is complementary to the 20 mer sequence from Nos. 540 to 459 of trh2-RNA.

The reaction solution was then incubated at 41° C. for 5 minutes, 0.1 U of RNase H (Takara Shuzo Co., Ltd.) was added (RNase H is an enzyme that cleaves the RNA of DNA/RNA double strands), and the PCR tube was incubated at 41° C. for 15 minutes.

Polyacrylamide gel (acrylamide concentration: 6%, urea: 7 M) electrophoresis was conducted to confirm the cleaved fragments after the reaction. Dyeing after electrophoresis was carried out with SYBR Green II (Takara Shuzo Co., Ltd.). Upon binding of the oligonucleotide to the specific site of the target RNA, the RNA of the DNA/RNA double strands is cleaved by RNase H and characteristic bands are observed.

Figure 3:
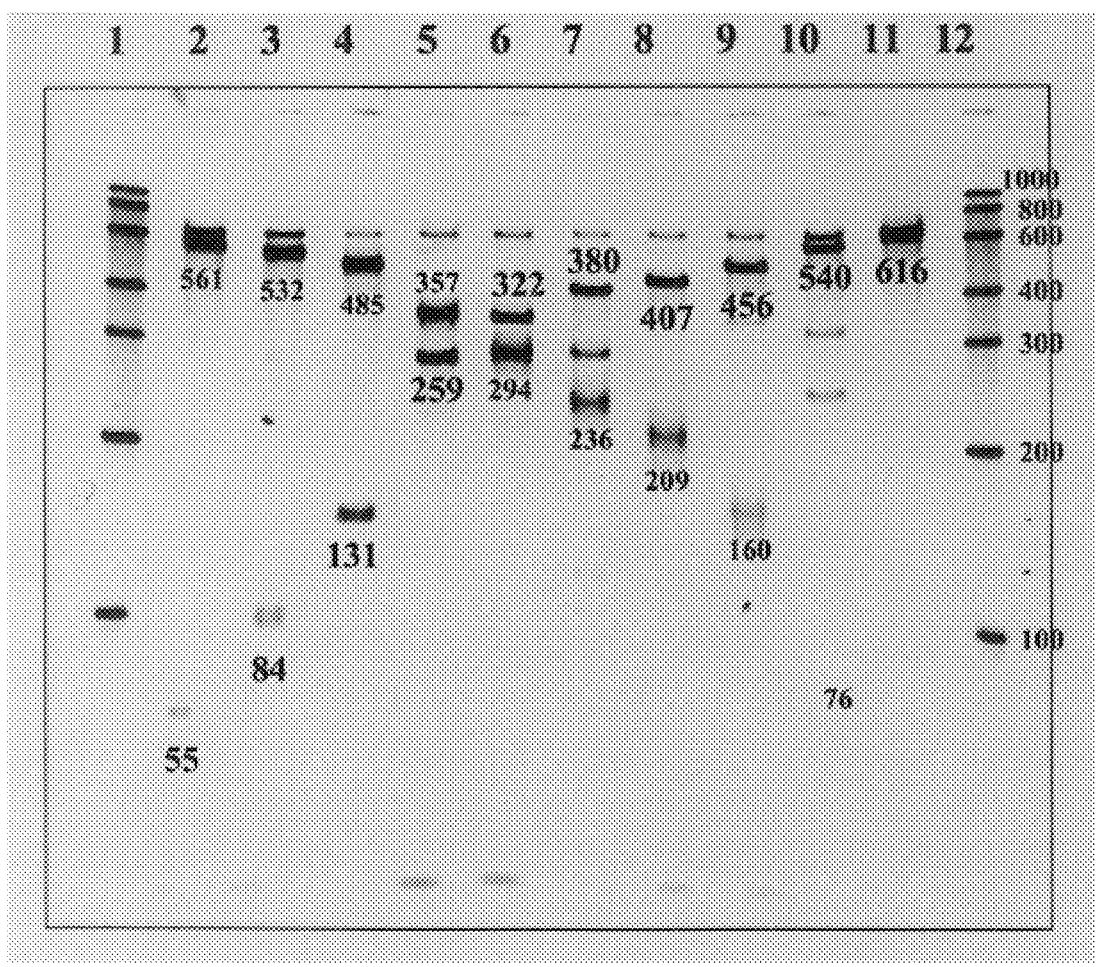
FIG. 3 illustrates an electrophoresis image of 6% PAGE for a sample after performing a binding test to trh2-RNA at 41° C., using oligonucleotides designed for an intramolecular structure-free region of trh2-RNA. In the image, lanes 1 and 12 are the RNA marker (0.1 to 1.0 K), lanes 2 to 10 relate to oligonucleotide solutions of SEQ. ID. No.6, 15, 7, 8, 16, 17, 9, 10 and 11, respectively, and lane 11 is a standard sample of trh2-RNA (616 mer).

The electrophoresis results are shown in FIG. 3 (FIG. 3 is a photograph showing the state of the oligonucleotides (black and white inverted)). The sizes of the newly appeared characteristic bands were as shown in FIG. 3. For example, in the experiment using the oligonucleotide of SEQ. ID. No.6, the sizes of the bands obtained by cleaving from the 55th base from the 5'-end of trh2-RNA, i.e. a 55 mer and a 56 mer, are shown.

Since characteristic bands were confirmed in the experiments using all of the aforementioned oligonucleotides in this manner, it was demonstrated that all of these oligonucleotides bind strongly to *Vibrio parahaemolyticus* trh2-RNA at 41° C.

Example 4

Specific binding of the oligonucleotides of the invention to trh1-RNA at 41° C. was examined.

First, a sample of a standard RNA (616 mer) comprising base Nos. 1 to 610 of trh1-RNA was quantified by ultraviolet absorption at 260 nm, and then diluted with a RNA diluent (10 mM Tris-HCl (pH 8.0), 0.1 mM EDTA, 0.5 U/µl RNase Inhibitor) to $3.0 \times 10^{-12}$ mol/µl.

Next, 14.0 µl of a reaction solution with the following composition was dispensed into a 0.5 ml volume PCR tube (GeneAmp Thin-Walled Reaction Tubes®; Perkin-Elmer Co., Ltd.).

Composition of Reaction Solution 20.0 mM Tris-HCl buffer (pH 7.5)
20.0 mM potassium chloride
10.0 mM magnesium chloride
0.1 mM DTT
0.1 mM EDTA
1.3 µM of oligonucleotide primer solution
$1.0 \times 10^{-12}$ mol standard trh2-RNA sample
Distilled water for volume adjustment As the oligonucleotide primer solutions, the oligonucleotide solution of SEQ. ID. No.6, the oligonucleotide solution of SEQ. ID. No.15, the oligonucleotide solution of SEQ. ID. No.7, the oligonucleotide solution of SEQ. ID. No.8, the oligonucleotide solution of SEQ. ID. No.16, the oligonucleotide solution of SEQ. ID. No.9 and the oligonucleotide solution of SEQ. ID. No.3 were used.

The reaction solution was then incubated at 41° C. for 5 minutes, 0.1 U of RNase H (Takara Shuzo Co., Ltd.) was added (RNase H is an enzyme that cleaves the RNA of DNA/RNA double strands), and the PCR tube was incubated at 41° C. for 15 minutes.

Polyacrylamide gel (acrylamide concentration: 6%, urea: 7 M) electrophoresis was conducted to confirm the cleaved fragments after the reaction. Dyeing after electrophoresis was carried out with SYBR Green II (Takara Shuzo Co., Ltd.). Upon binding of the oligonucleotide to the specific site of the target RNA, the RNA of the DNA/RNA double strands is cleaved by RNase H and characteristic bands are observed.

Figure 4:
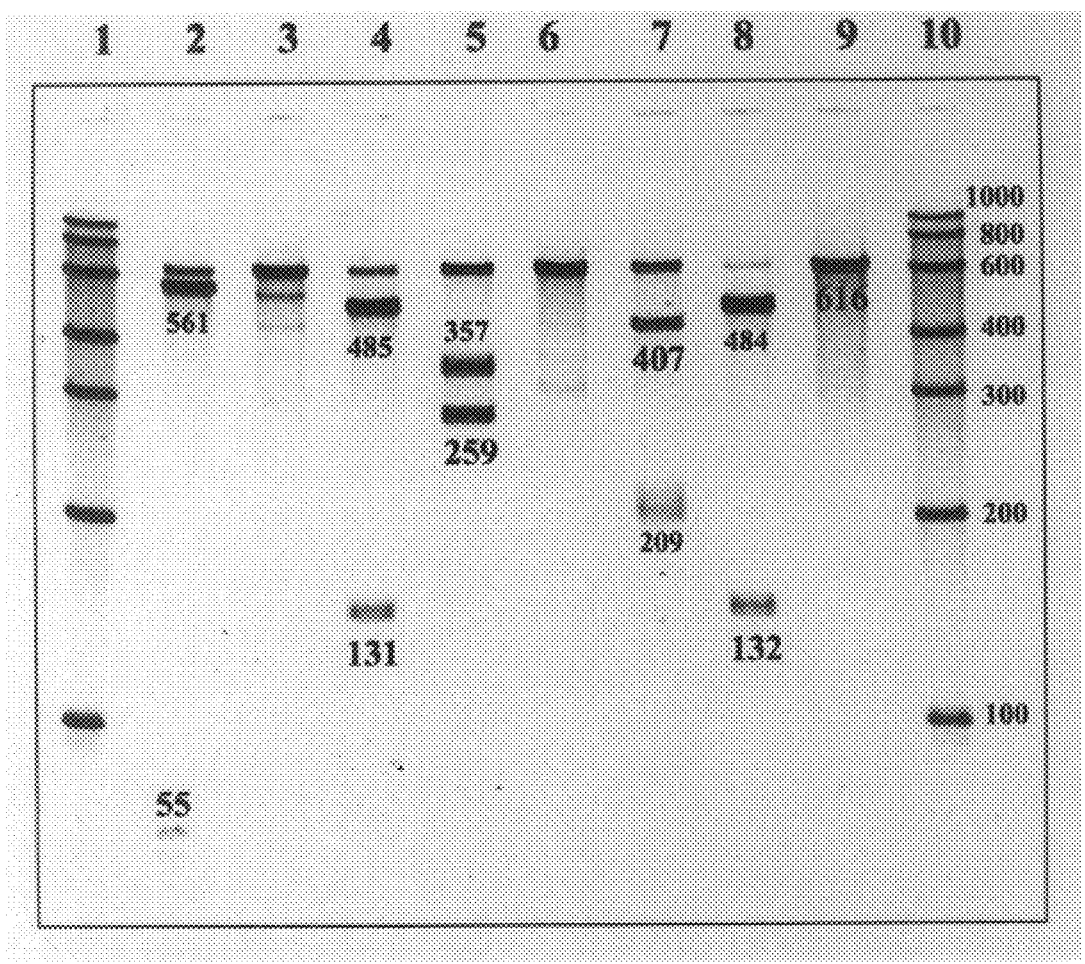
FIG. 4 illustrates an electrophoresis image of 6% PAGE for a sample after performing a binding test with trh1-RNA at 41° C., using oligonucleotides designed for an intramolecular structure-free region of trh2-RNA. In the image, lanes 1 and 10 are the RNA marker (0.1 to 1.0 K), lanes 2 to 8 relate to oligonucleotide solutions of SEQ. ID. No.6, 15, 7, 8, 16, 9 and 3, respectively, and lane 9 is a standard sample of trh1-RNA (616 mer).

The electrophoresis results are shown in FIG. 4 (FIG. 4 is a photograph showing the state of the oligonucleotides (black and white inverted)). The sizes of the newly appeared characteristic bands were as shown in FIG. 4. For example, in the experiment using the oligonucleotide of SEQ. ID. No.6, the sizes of the bands obtained by cleaving from the 55th base from the 5'-end of trh2-RNA, i.e. a 55 mer and a 561 mer, are shown.

Since characteristic bands were confirmed in the experiments using the oligonucleotides of SEQ. ID. No.6, SEQ. ID. No.7, SEQ. ID. No.8 and SEQ. ID. No.9 in this manner, it was demonstrated that the oligonucleotides with these sequences bind strongly to *Vibrio parahaemolyticus* trh1-RNA at 41° C. On the other hand, the oligonucleotides of SEQ. ID. No.15 and SEQ. ID. No.16 did not bind to the trh1-RNA. The oligonucleotide of SEQ. ID. No.3 was used as a control sequence that binds strongly to trh1-RNA at 41° C. In light of the results of Example 3, it was demonstrated that the oligonucleotides of SEQ. ID. No.6, SEQ. ID. No.7, SEQ. ID. No.8 and SEQ. ID. No.9 bind strongly to both trh1-RNA and trh2-RNA at 41° C. On the other hand, it was demonstrated that the oligonucleotides of SEQ. ID. No.15 and SEQ. ID. No.16 bind strongly only to trh2-RNA at 41° C.

Example 5

Specific binding of the oligonucleotides of the invention to trh1-RNA or trh2-RNA at 41° C. was examined.

First, a sample of a standard RNA (616 mer) comprising base Nos. 1 to 610 of trh1-RNA or trh2-RNA was quantified by ultraviolet absorption at 260 nm, and then diluted with a RNA diluent (10 mM Tris-HCl (pH 8.0), 0.1 mM EDTA, 0.5 U/µl RNase Inhibitor) to $3.0 \times 10^{-12}$ mol/µl.

Next, 14.0 µl of a reaction solution with the following composition was dispensed into a 0.5 ml volume PCR tube (GeneAmp Thin-Walled Reaction Tubes®; Perkin-Elmer Co., Ltd.).

Composition of Reaction Solution 20.0 mM Tris-HCl buffer (pH 7.5)
20.0 mM potassium chloride
10.0 mM magnesium chloride
0.1 mM DTT
0.1 mM EDTA
1.3 µM of oligonucleotide primer solution
$1.0 \times 10^{-12}$ mol standard trh2-RNA sample
Distilled water for volume adjustment As the oligonucleotide primer solutions, the oligonucleotide solution of SEQ. ID. No.17, the oligonucleotide solution of SEQ. ID. No.10, the oligonucleotide solution of SEQ. ID. No.11 and the oligonucleotide solution of SEQ. ID. No.4 were used.

The reaction solution was then incubated at 41° C. for 5 minutes, 0.1 U of RNase H (Takara Shuzo Co., Ltd.) was added (RNase H is an enzyme that cleaves the RNA of DNA/RNA double strands), and the PCR tube was incubated at 41° C. for 15 minutes.

Polyacrylamide gel (acrylamide concentration: 6%, urea: 7 M) electrophoresis was conducted to confirm the cleaved fragments after the reaction. Dyeing after electrophoresis was carried out with SYBR Green II (Takara Shuzo Co., Ltd.). Upon binding of the oligonucleotide to the specific site of the target RNA, the RNA of the DNA/RNA double strands is cleaved by RNase H and characteristic bands are observed.

Figure 5:
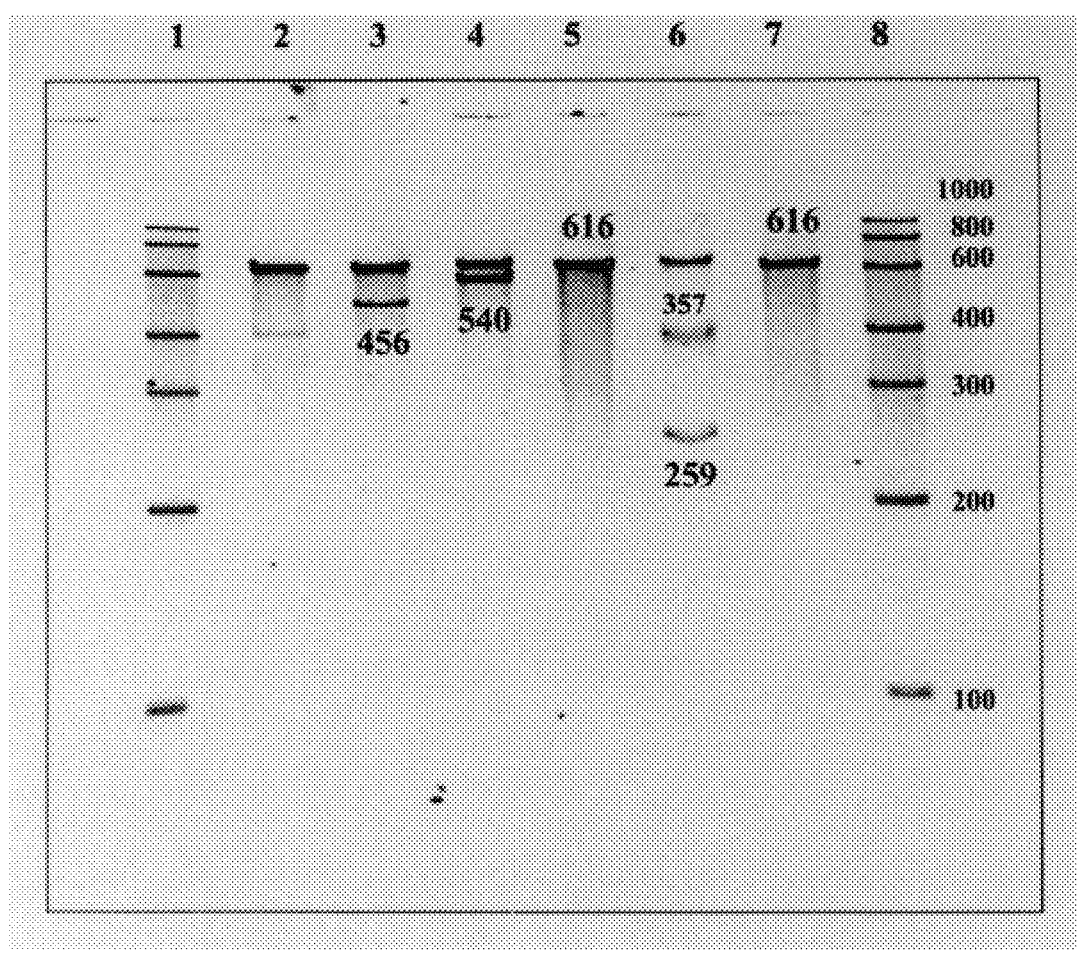
FIG. 5 illustrates an electrophoresis image of 6% PAGE for a sample after performing a binding test to trh1-RNA at 41° C., using oligonucleotides designed for an intramolecular structure-free region of trh1-RNA, and for a sample after performing a binding test to trh2-RNA at 41° C., using oligonucleotides designed for an intramolecular structure-free region of trh1-RNA. In the image, lanes 1 and 8 are the RNA marker (0.1 to 1.0 K), lanes 2 to 4 relate to oligonucleotide solutions of SEQ. ID. No.17, 10 and 11, respectively, and lane 5 is a standard sample of trh1-RNA (616 mer). Lane 6 relates to an oligonucleotide solution of SEQ. ID. No.4, and lane 7 is a standard sample of trh2-RNA (616 mer).

The electrophoresis results are shown in FIG. 5 (FIG. 5 is a photograph showing the state of the oligonucleotides (black and white inverted)). The sizes of the newly appeared characteristic bands were as shown in FIG. 5. For example, in the experiment using the oligonucleotide of SEQ. ID. No.10, the sizes of the bands obtained by cleaving from the 456th base from the 5'-end of trh2-RNA, i.e. a 456 mer and a 160 mer, are shown.

Since characteristic bands were confirmed in the experiments using the oligonucleotides of SEQ. ID. No.10 and SEQ. ID. No.11 in this manner, it was demonstrated that the oligonucleotides with these sequences bind strongly to *Vibrio parahaemolyticus* trh1-RNA at 41° C. On the other hand, the oligonucleotide of SEQ. ID. No.17 did not bind to the trh1-RNA. In light of the results of Example 3, it was demonstrated that the oligonucleotides of SEQ. ID. No.10 and SEQ. ID. No.11 bind strongly to both trh1-RNA and trh2-RNA at 41° C. On the other hand, it was demonstrated that the oligonucleotide of SEQ. ID. No.17 binds strongly only to trh2-RNA at 41° C. Since a characteristic band was confirmed in the experiment using the oligonucleotide of SEQ. ID. No.4, it was demonstrated that the oligonucleotide of SEQ. ID. No.4 binds strongly to *Vibrio parahaemolyticus* trh2-RNA at 41° C. In light of the results of Example 1, it was demonstrated that the oligonucleotide of SEQ. ID. No.4 binds strongly to both trh1-RNA and trh2-RNA at 41° C.

Results

As explained above, the oligonucleotides of the present invention are oligonucleotides that complementarily bind to RNA derived from *Vibrio parahaemolyticus* trh1 and/or trh2, even under conditions of relatively low and constant temperature (35–50° C., preferably 41° C.), which tend to produce an intramolecular structure in RNA and prevent binding of primers and probes thereto. Specific binding of the oligonucleotides is therefore possible without heat denaturation of the target RNA. The oligonucleotides of the invention are thus useful as oligonucleotides for amplification or detection of RNA derived from the *Vibrio parahaemolyticus* thermostable direct hemolysin-related hemolysin genes (trh1 or trh2), i.e. as oligonucleotide primers or oligonucleotide probes to be used in RNA amplification methods.

Furthermore, the oligonucleotides of the invention are also clearly useful for amplification and detection of trh1 and trh2. Oligonucleotides complementary to the above-mentioned oligonucleotides are also useful for amplification of double-stranded DNA by the PCR method, or for detection of cDNA obtained by reverse transcription of RNA.

The oligonucleotides of the invention are not limited to the specifically listed 20 mers, and they also include oligonucleotides comprising at least 10 or more contiguous bases within those sequences. This is obvious from the fact that 10 mer base sequences are sufficient to ensure adequate specificity of primers or probes to target nucleic acids.

2. Oligonucleotide Which Complementarily Binds to RNA Derived from tdh2

Example 6

Specific binding of the oligonucleotides of the invention to tdh2-RNA at 41° C. was examined. The tdh2-RNA is a synthesized and purified RNA obtained by in vitro transcription using double-stranded DNA containing the tdh2 base sequence as the template.

First, a sample of a standard RNA (616 mer) comprising base Nos. 1 to 610 of *Vibrio parahaemolyticus* tdh2-RNA (the RNA base sequence numbering is in accordance with Nishibuchi et al. "Appl. Environ. Microbiol., 1992, 58, pp.2449–2457") was quantified by ultraviolet absorption at 260 nm, and then diluted with a RNA diluent (10 mM Tris-HCl (pH 8.0), 0.1 mM EDTA, 0.5 U/$\mu$l RNase Inhibitor) to $3.0 \times 10^{-12}$ mol/$\mu$l.

Next, 14.0 $\mu$l of a reaction solution with the following composition was dispensed into a 0.5 ml volume PCR tube (GeneAmp Thin-Walled Reaction Tubes®; Perkin-Elmer Co., Ltd.).

Composition of Reaction Solution 20.0 mM Tris-HCl buffer (pH 7.5)
20.0 mM potassium chloride
10.0 mM magnesium chloride
0.1 mM DTT
0.1 mM EDTA
1.3 $\mu$M of oligonucleotide primer solution
$1.0 \times 10^{-12}$ mol standard tdh2-RNA sample
Distilled water for volume adjustment As the oligonucleotide primer solutions, oligonucleotide solutions of SEQ. ID. Nos.18 to 24 were used. In this context, the oligonucleotide of SEQ. ID. No.18 is complementary to the 20 mer sequence from Nos. 66 to 85 of tdh2-RNA, the oligonucleotide of SEQ. ID. No.19 is complementary to the 20 mer sequence from Nos. 162 to 181 of tdh2-RNA, the oligonucleotide of SEQ. ID. No.20 is complementary to the 20 mer sequence from Nos. 241 to 260 of tdh2-RNA, the oligonucleotide of SEQ. ID. No.21 is complementary to the 20 mer sequence from Nos. 275 to 294 of tdh2-RNA, the oligonucleotide of SEQ. ID. No.22 is complementary to the 20 mer sequence from Nos. 399 to 418 of tdh2-RNA, the oligonucleotide of SEQ. ID. No.23 is complementary to the 20 mer sequence from Nos. 453 to 472 of tdh2-RNA, and the oligonucleotide of SEQ. ID. No.24 is complementary to the 20 mer sequence from Nos. 540 to 559 of tdh2-RNA.

The reaction solution was then incubated at 41° C. for 5 minutes, 0.1 U of RNase H (Takara Shuzo Co., Ltd.) was added (RNase H is an enzyme that cleaves the RNA of DNA/RNA double strands), and the PCR tube was incubated at 41° C. for 15 minutes.

Polyacrylamide gel (acrylamide concentration: 6%, urea: 7 M) electrophoresis was conducted to confirm the cleaved fragments after the reaction. Dyeing after electrophoresis was carried out with SYBR Green II (Takara Shuzo Co., Ltd.). Upon binding of the oligonucleotide to the specific site of the target RNA, the RNA of the DNA/RNA double strands is cleaved by RNase H and characteristic bands are observed.

Figure 6:
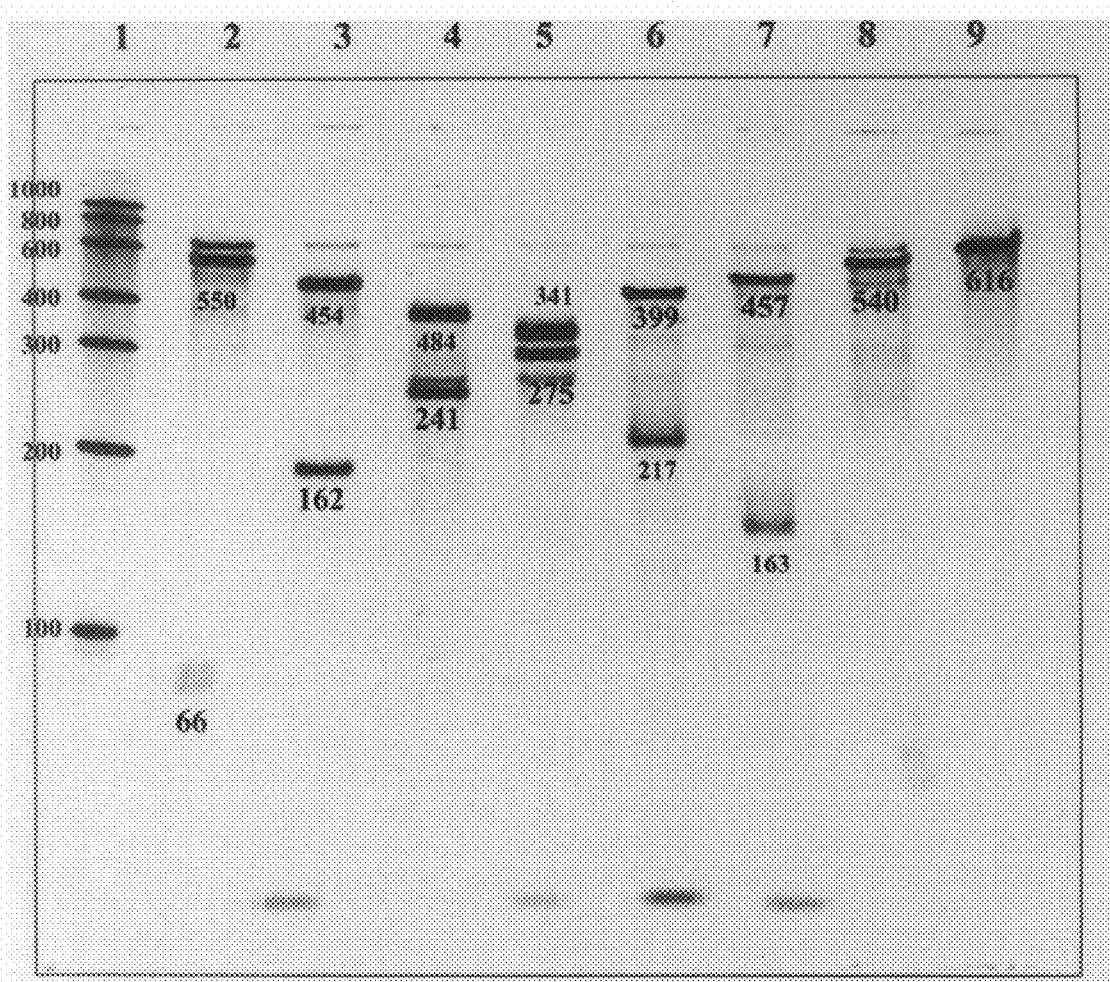
FIG. 6 illustrates an electrophoresis image of 6% PAGE for a sample after performing a binding test to tdh2-RNA at 41° C., using oligonucleotides designed for an intramolecular structure-free region of tdh2-RNA. In the image, lane 1 is the RNA marker (0.1 to 1.0 K), lanes 2 to 8 relate to oligonucleotide solutions of SEQ. ID. No.18 to 24, respectively, and lane 9 is a standard sample of tdh2-RNA (616 mer).

The electrophoresis results are shown in FIG. 6 (FIG. 6 is a photograph showing the state of the oligonucleotides (black and white inverted)). The sizes of the newly appeared characteristic bands were as shown in FIG. 6. For example, in the experiment using the oligonucleotide of SEQ. ID. No.18, the sizes of the bands obtained by cleaving from the 66th base from the 5'-end of tdh2-RNA, i.e. a 66 mer and a 550 mer, are shown. Since characteristic bands were confirmed in the experiments using all of the aforementioned oligonucleotides in this manner, it was demonstrated that all of these oligonucleotides bind strongly to *Vibrio parahaemolyticus* tdh2-RNA at 41° C.

Results

As explained above, the oligonucleotides of the present invention are oligonucleotides that complementarily bind to RNA derived from *Vibrio parahaemolyticus* tdh2, even under conditions of relatively low and constant temperature (35–50° C., preferably 41° C.), which tend to produce an intramolecular structure in RNA and prevent binding of primers and probes thereto. Specific binding of the oligonucleotides is therefore possible without heat denaturation of the target RNA. The oligonucleotides of the invention are thus useful as oligonucleotides for amplification or detection of RNA derived from the *Vibrio parahaemolyticus* thermostable direct hemolysin gene (tdh2), i.e. as oligonucleotide primers or oligonucleotide probes to be used in RNA amplification methods.

Furthermore, the oligonucleotides of the invention are also clearly useful for amplification and detection of tdh2. Oligonucleotides complementary to the above-mentioned specific oligonucleotides are also useful for amplification of double-stranded DNA by the PCR method, or for detection of cDNA obtained by reverse transcription of RNA.

The oligonucleotides of the invention are not limited to the specifically listed 20 mers, and they also include oligonucleotides comprising at least 10 or more contiguous bases within those sequences. This is obvious from the fact that about 10 mer base sequences are sufficient to ensure adequate specificity of primers or probes to target nucleic acids.

3. Detection and Amplification of RNA derived from trh1

Example 7

A combination of oligonucleotide primers according to the invention was used for specific amplification of a target RNA. Trh1-RNA is a synthesized and purified RNA obtained by in vitro transcription using double-stranded DNA containing the trh1 base sequence as the template. Similarly, trh2-RNA and tdh2-RNA were prepared by in vitro transcription.

(1) A sample of a standard RNA (616 mer) comprising base Nos. 1 to 610 of *Vibrio parahaemolyticus* trh1-RNA (the RNA base sequence numbering is in accordance with Nishibuchi et al. *Appl. Environ. Microbiol.,* 58, pp.2449–2457, 1992) was quantified by ultraviolet absorption at 260 nm, and then diluted with a RNA diluent (10 mM Tris-HCl (pH 8.0), 0.1 mM EDTA, 0.5 U/$\mu$l RNase Inhibitor, 5.0 mM DDT) to $1.0 \times 10^4$ copies/5 $\mu$l and $1.0 \times 10^3$ copies/5 $\mu$l. The diluent alone was used as a control test group (Nega).

(2) 20.8 $\mu$l of a reaction solution with the following composition was dispensed into a commercially available 0.5 ml volume PCR tube (GeneAmp Thin-Walled Reaction Tubes®; Perkin-Elmer Co., Ltd.), and 5.0 $\mu$l of the RNA sample was added thereto.

Composition of reaction solution (Final concentrations in reaction system after enzyme solution addition)

60.0 mM Tris-HCl buffer (pH 8.6)
13.0 mM magnesium chloride
90.0 mM potassium chloride
1.0 mM DTT
0.25 mM each of dATP, dCTP, dGTP, dTTP
3.0 mM each of ATP, CTP, UTP 2.25 mM GTP 3.6 mM ITP 1.0 μM each of first primer and second primer (The primer combinations were as shown in Table 1, where the portions from the first "A" to the 28th "A" from the 5'-end in the sequences of SEQ. ID. Nos.28 and 29 are the sequence added as the T7 polymerase promoter sequence).

0.16 μM of cleaving oligonucleotide primer (SEQ. ID. No.27; an oligonucleotide which cleaves the target RNA at the site where the second primer may bind; 3'-end thereof had been aminated)

39 U of Ribonuclease Inhibitor (Takara Shuzo Co., Ltd.)

15.0% DMSO

Distilled water for volume adjustment

TABLE 1

| Combination | First primer | Second primer | Cleaving primer |
|---|---|---|---|
| [1] | SEQ.ID.No.25 | SEQ.ID.No.28 | SEQ.ID.No.27 |
| [2] | SEQ.ID.No.25 | SEQ.ID.No.29 | SEQ.ID.No.27 |

(3) The reaction solution was incubated at 41° C. for 5 minutes, and then 4.2 μl of an enzyme solution pre-incubated at 41° C. for 2 minutes was added thereto.

Composition of enzyme solution (final concentrations at time of reaction)

1.7% sorbitol 8 units of AMV reverse transcriptase (Takara Shuzo Co., Ltd.)

142 units of T7 RNA polymerase (GIBCO Corp.)

3 μg of bovine serum albumin

Distilled water for volume adjustment (4) After incubating the PCR tube at 41° C. for 30 minutes, the specific amplification product was analyzed by electrophoresis using 4% agarose gel.

(5) Dyeing after electrophoresis was carried out using a commercially available dyeing solution (SYBR Green II, TM of Takara Shuzo Co., Ltd.).

The electrophoresis results are shown in FIG. 7 (black and white inverted). Both of the combinations resulted specific RNA amplification products in trh1-RNA-added systems (arrow-indicated sections of FIG. 7). No amplification product was obtained, however, in tdh2-RNA and trh2-RNA-added systems. This indicated that these oligonucleotide primer combinations are useful for the amplification and detection of RNA derived from the *Vibrio parahaemolyticus* thermostable direct hemolysin-related hemolysin gene (trh1).

Results

As explained above, the present invention provides combinations of oligonucleotide primers and oligonucleotide probes which bind specifically to RNA derived from a *Vibrio parahaemolyticus* thermostable direct hemolysin-related hemolysin gene (trh1) even under conditions of relatively low and constant temperature (35–50° C., preferably 41° C.), which tend to cause RNA in samples to form an intramolecular structure and prevent binding of primers and probes thereto, and they are therefore useful for rapid amplification and detection of target RNA.

Furthermore, the oligonucleotide combinations of the invention are not limited to thr1-RNA, since the complementary sequences of these oligonucleotides are useful for detection of cDNA obtained by reverse transcription of the RNA.

The base lengths of the oligonucleotides in the combinations of the invention are not limited to the listed lengths, and they also include oligonucleotides comprising at least 10 or more contiguous bases within those sequences. This is obvious from the fact that base sequences comprising about 10 bases are sufficient to ensure adequate specificity of primers or probes to target nucleic acids.

4. Detection and Amplication of RNA derived from trh2

Example 8

A combination of oligonucleotide primers according to the invention was used for specific amplification of target RNA. The trh2-RNA is a synthesized and purified RNA obtained by in vitro transcription using double-stranded DNA containing the trh2 base sequence as the template. Similarly, trh1-RNA and tdh2-RNA were prepared by in vitro transcription.

(1) A sample of a standard RNA (616 mer) comprising base Nos. 1 to 610 of *Vibrio parahaemolyticus* trh2-RNA (the RNA base sequence numbering is in accordance with Nishibuchi et al. Appl. Environ. Microbiol., 58, pp.2449–2457, 1992) was quantified by ultraviolet absorption at 260 nm, and then diluted with a RNA diluent (10 mM Tris-HCl (pH 8.0), 0.1 mM EDTA, 0.5 U/μl RNase Inhibitor, 5.0 mM DDT) to $1.0 \times 10^4$ copies/5 μl and $1.0 \times 10^3$ copies/5 μl. The diluent alone was used as a control test group (Nega).

(2) 20.8 μl of a reaction solution with the following composition was dispensed into a commercially available 0.5 ml volume PCR tube (GeneAmp Thin-Walled Reaction Tubes®; Perkin-Elmer Co., Ltd.), and 5.0 μl of the RNA sample was added thereto.

Composition of Reaction Solution (Final Concentrations in Reaction System After Enzyme Solution Addition)

60.0 mM Tris-HCl buffer (pH 8.6)

13.0 mM magnesium chloride 90.0 mM potassium chloride 1.0 mM DTT 0.25 mM each of dATP, dCTP, dGTP, dTTP 3.0 mM each of ATP, CTP, UTP 2.25 mM GTP 3.6 mM ITP 1.0 μM each of first primer and second primer (The primer combinations were as shown in Table 2, where the portions from the first "A" to the 28th "A" from the 5'-end in the sequences of SEQ. ID. Nos.36 and 37 are the sequences added as the T7 polymerase promoter sequence).

0.16 μM of cleaving oligonucleotide primer (SEQ. ID. No.35; an oligonucleotide which cleaves the target RNA at the site where the second primer may bind; 3'-end thereof had been aminated)

39 U of Ribonuclease Inhibitor (Takara Shuzo Co., Ltd.)

15.0% DMSO

Distilled water for volume adjustment

TABLE 2

| Combination | First primer | Second primer | Cleaving primer |
|---|---|---|---|
| [1] | SEQ.ID.No.33 | SEQ.ID.No.36 | SEQ.ID.No.35 |
| [2] | SEQ.ID.No.33 | SEQ.ID.No.37 | SEQ.ID.No.35 |

(3) The reaction solution was incubated at 41° C. for 5 minutes, and then 4.2 μl of enzyme solution pre-incubated at 41° C. for 2 minutes was added thereto.

Composition of Enzyme Solution (Final Concentrations at Time of Reaction)

1.7% sorbitol 8 units of AMV reverse transcriptase (Takara Shuzo Co., Ltd.)

142 units of T7 RNA polymerase (GIBCO Corp.)

3 μg of bovine serum albumin

Distilled water for volume adjustment (4) After incubating the PCR tube at 41° C. for 30 minutes, the specific amplification product was analyzed by electrophoresis using 4% agarose gel.

(5) Dyeing after electrophoresis was carried out using a commercially available dyeing solution (SYBR Green II, TM of Takara Shuzo Co., Ltd.).

The electrophoresis results are shown in FIG. 8 (black and white inverted). Both of the combinations resulted in specific RNA amplification products in trh2-RNA-added systems (arrow-indicated sections of FIG. 8). No amplification product was obtained, however, in tdh2-RNA and trh1-RNA-added systems. This indicated that these oligonucleotide primer combinations are useful for the amplification and detection of RNA derived from the *Vibrio parahaemolyticus* thermostable direct hemolysin-related hemolysin gene (trh2).

Results

As explained above, the present invention provides combinations of oligonucleotide primers and oligonucleotide probes which bind specifically to RNA derived from a *Vibrio parahaemolyticus* thermostable direct hemolysin-related hemolysin gene (trh2) even under conditions of relatively low and constant temperature (35–50° C., preferably 41° C.), which tend to cause RNA in samples to form an intramolecular structure and prevent binding of primers and probes thereto, and they are therefore useful for rapid amplification and detection of target RNA.

Furthermore, the oligonucleotide combinations of the invention are not limited to thr2-RNA, since the complementary sequences of these oligonucleotides are useful for detection of cDNA obtained by reverse transcription of the RNA.

The base lengths of the oligonucleotides in the combinations of the invention are not limited to the listed lengths, and they also include oligonucleotides comprising at least 10 or more contiguous bases within those sequences. This is obvious from the fact that base sequences comprising about 10 bases are sufficient to ensure adequate specificity of primers or probes to target nucleic acids.

5. Detection and Amplification of RNA derived from tdh2

Example 9

A combination of oligonucleotide primers according to the invention was used for specific amplification of target RNA. Tdh2-RNA is a synthesized and purified RNA obtained by in vitro transcription using double-stranded DNA containing the tdh2 base sequence as the template.

(1) A sample of a standard RNA (616 mer) comprising base Nos. 1 to 610 of *Vibrio parahaemolyticus* tdh2-RNA (the RNA base sequence numbering is in accordance with Nishibuchi et al. Appl. Environ. Microbiol., 58, pp.2449–2457, 1992) was quantified by ultraviolet absorption at 260 nm, and then diluted with a RNA diluent (10 mM Tris-HCl (pH 8.0), 0.1 mM EDTA, 0.5 U/μl RNase Inhibitor, 5.0 mM DDT) to $1.0 \times 10^5$ copies/5μl. The diluent alone was used as a control test group (Nega).

(2) 20.8 μl of a reaction solution with the following composition was dispensed into a commercially available 0.5 ml volume PCR tube (GeneAmp Thin-Walled Reaction Tubes, TM of Perkin-Elmer Co., Ltd.), and 5.0 μl of the RNA sample was added thereto.

Composition of Reaction Solution (Final Concentrations in Reaction System After Enzyme Solution Addition)

60.0 mM Tris-HCl buffer (pH 8.6)

13.0 mM magnesium chloride 90.0 mM potassium chloride 1.0 mM DTT 0.25 mM each of dATP, dCTP, dGTP, dTTP 3.0 mM each of ATP, CTP, UTP 2.25 mM GTP 3.6 mM ITP 1.0 μM of first primer 1.0 μM of second primer (The portions from the first "A" to the 28th "A" from the 5'-end in the sequences of SEQ. ID. Nos.43, 45, 46 and 48, respectively, are sequences added as the T7 polymerase promoter sequence).

0.16 μM of cleaving oligonucleotide primer (an oligonucleotide which cleaves the target RNA at the site where the second primer may bind; 3'-end thereof had been aminated)

(The primer combinations were as shown in Table 3)

39 U of Ribonuclease Inhibitor (Takara Shuzo Co., Ltd.)

15.0% DMSO

Distilled water for volume adjustment

TABLE 3

| Combination | First primer | Second primer | Cleaving primer |
|---|---|---|---|
| [1] | SEQ.ID.No.39 | SEQ.ID.No.43 | SEQ.ID.No.44 |
| [2] | SEQ.ID.No.39 | SEQ.ID.No.45 | SEQ.ID.No.44 |
| [3] | SEQ.ID.No.39 | SEQ.ID.No.46 | SEQ.ID.No.47 |
| [4] | SEQ.ID.No.39 | SEQ.ID.No.48 | SEQ.ID.No.47 |
| [5] | SEQ.ID.No.42 | SEQ.ID.No.46 | SEQ.ID.No.47 |
| [6] | SEQ.ID.No.42 | SEQ.ID.No.48 | SEQ.ID.No.47 |

(3) The reaction solution was incubated at 41° C. for 5 minutes, and then 4.2 μl of enzyme solution pre-incubated at 41° C. for 2 minutes was added thereto.

Composition of Enzyme Solution (Final Concentrations at Time of Reaction)

1.7% sorbitol 8 units of AMV reverse transcriptase (Takara Shuzo Co., Ltd.)

142 units of T7 RNA polymerase (GIBCO Corp.)

3 µg of bovine serum albumin

Distilled water for volume adjustment (4) After incubating the PCR tube at 41° C. for 30 minutes, the specific amplification product was analyzed by electrophoresis using 3% agarose gel.

(5) Dyeing after electrophoresis was carried out using a commercially available dyeing solution (SYBR Green II, TM of Takara Shuzo Co., Ltd.).

The electrophoresis results are shown in FIG. 9 (black and white inverted). Both of the combinations resulted specific RNA amplification products(arrow-indicated sections of FIG. 9). This indicated that these oligonucleotide primer combinations are useful for the amplification and detection of RNA derived from tdh2.

Example 10

A combination of oligonucleotide primers according to the invention was used for specific detection of different initial copy numbers of target tdh2-RNA.

(1) A sample of a standard RNA (616 mer) comprising base Nos. 1 to 610 of *Vibrio parahaemolyticus* tdh2-RNA (the RNA base sequence numbering is in accordance with Nishibuchi et al. Appl. Environ. Microbiol., 58, pp.2449–2457, 1992) was quantified by ultraviolet absorption at 260 nm, and then diluted with a RNA diluent (10 mM Tris-HCl (pH 8.0), 0.1 mM EDTA, 0.5 U/µl RNase Inhibitor, 5.0 mM DDT) to from $1.0 \times 10^5$ copies/5 µl to $1.0 \times 10^2$ copies/5 µl. The diluent alone was used as a control test group (Nega).

(2) 20.8 µl of a reaction solution with the following composition was dispensed into a commercially available 0.5 ml volume PCR tube (GeneAmp Thin-Walled Reaction Tubes®; Perkin-Elmer Co., Ltd.), and 5 µl of the RNA sample was added.

Composition of Reaction Solution (Final
Concentrations in Reaction System After Enzyme
Solution Addition)

60.0 mM Tris-HCl buffer (pH 8.6)

13.0 mM magnesium chloride 90.0 mM potassium chloride 1.0 mM DTT 0.25 mM each of dATP, dCTP, dGTP, dTTP 3.0 mM each of ATP, CTP, UTP 2.25 mM GTP 3.6 mM ITP 1.0 µM of first oligonucleotide primer (SEQ. ID. No.42)

1.0 µM of second oligonucleotide primer (SEQ. ID. No.48)

(The portion from the first "A" to the 28th "A" from the 5'-end in SEQ. ID. No.48 is the sequence added as the T7 polymerase promoter sequence).

0.8 µM of cleaving oligonucleotide primer (SEQ. ID. No.47; an oligonucleotide which cleaves the target RNA at the site where the second primer may bind; 3'-end thereof had been aminated)

39 U of Ribonuclease Inhibitor (Takara Shuzo Co., Ltd.)

15.0% DMSO

Figure 10:
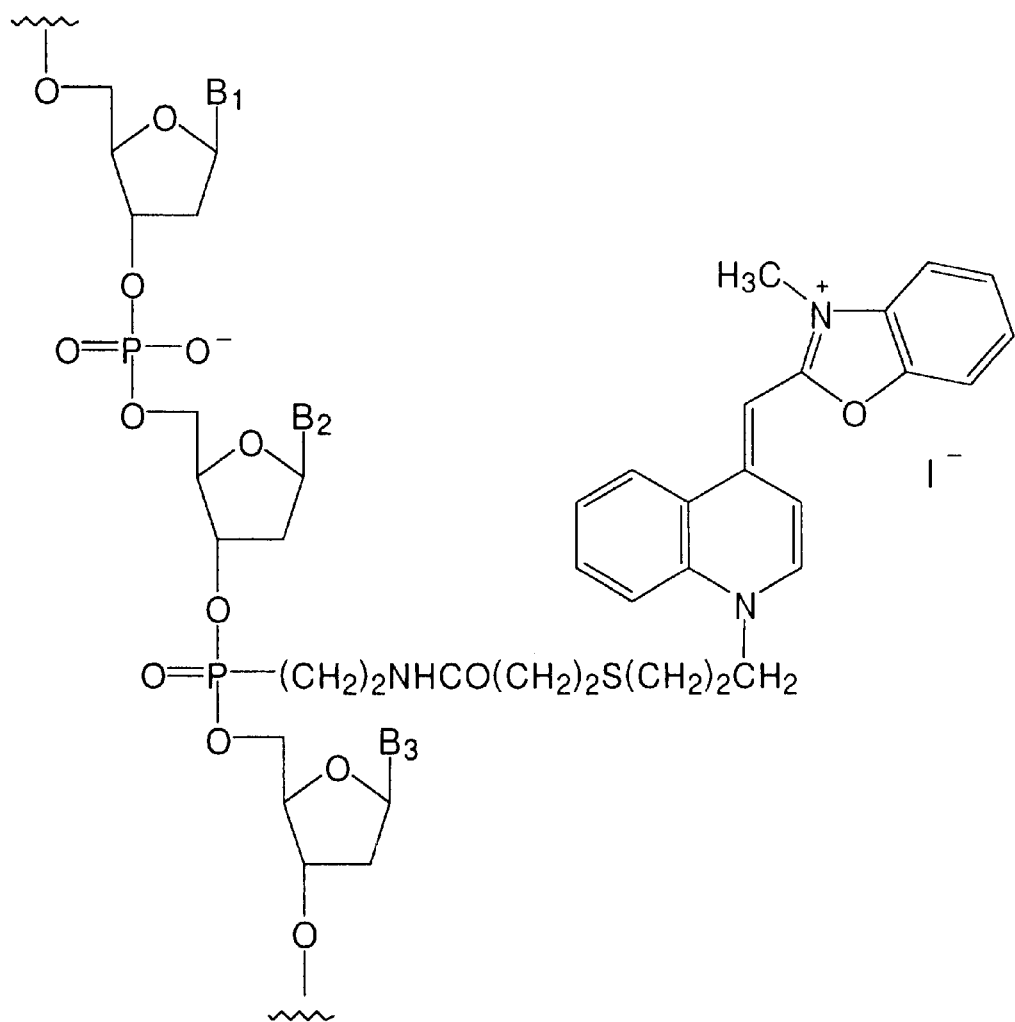
FIG. 10 shows the chemical structures of the intercalator fluorescent dye portions of the oligonucleotides labeled with the intercalator fluorescent dye used in Examples 10 and 11. $B_1$–$B_3$ represent nucleic acid bases.

Distilled water for volume adjustment 25.0 nM of oligonucleotide probe labeled with intercalator fluorescent dye (FIG. 10) (TDH-YO) (The oligonucleotide sequence is SEQ. ID. No.39 modified with glycolic acid at the 3'-end).

39 units of Ribonuclease Inhibitor (Takara Shuzo Co., Ltd.)

15.0% DMSO

Distilled water for volume adjustment (3) The reaction solution was incubated at 41° C. for 5 minutes, and then 4.2 µl of enzyme solution pre-incubated at 41° C. for 2 minutes was added thereto.

Composition of Enzyme Solution (Final
Concentrations at time of reaction)

1.7% sorbitol 8 units of AMV reverse transcriptase (Takara Shuzo Co., Ltd.)

142 units of T7 RNA polymerase (GIBCO Corp.)

3 µg of bovine serum albumin

Figure 11:
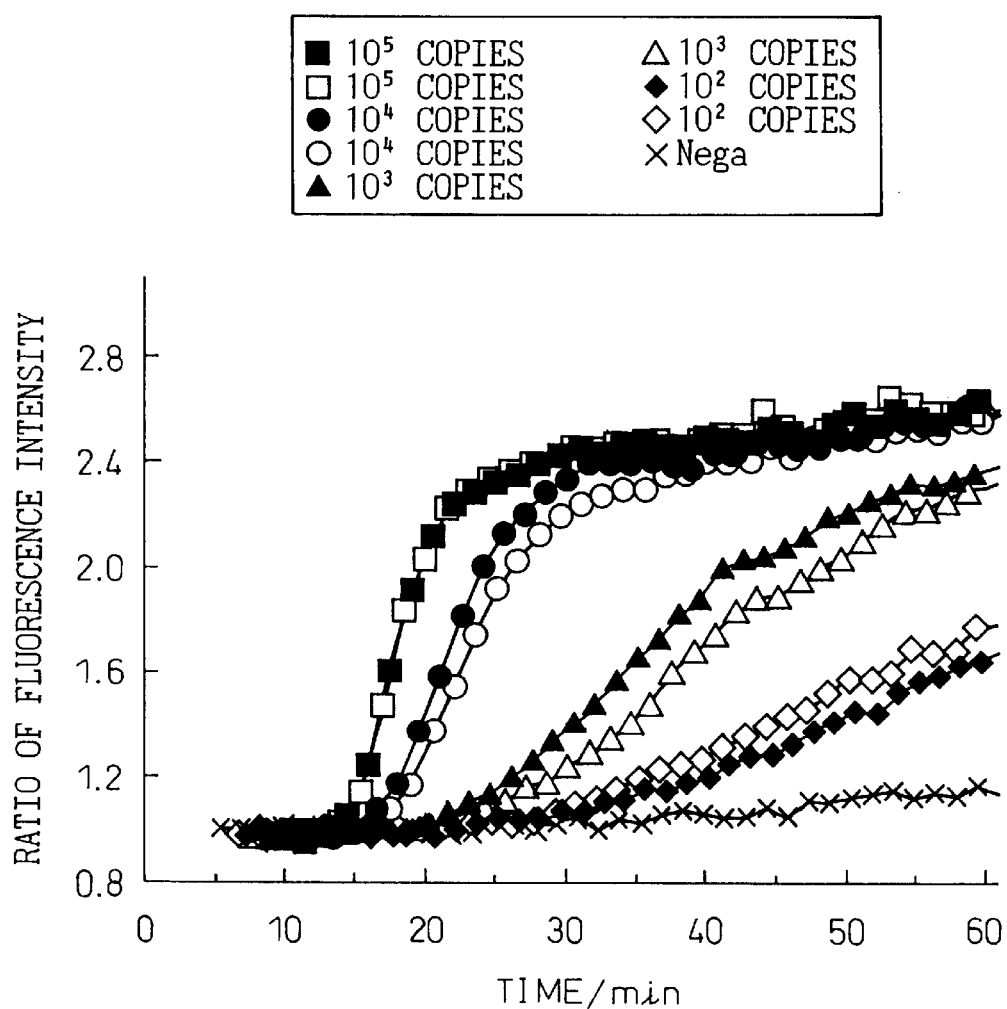
FIG. 11 illustrates the result of Example 10, showing the increase of fluorescence rate with the reaction time and the RNA production, at an initial RNA amount of $10^5$ copies/30 $\mu$l to $10^2$ copies/30 $\mu$l. "Nega" represents the results using the diluent alone instead of a RNA sample.

Distilled water for volume adjustment (4) Next, using a temperature-controllable fluorescent spectrophotometer capable of directly measuring PCR tubes, periodic measurement of the fluorescence intensity of the reaction solution incubated at 41° C. with an excitation wavelength of 470 nm and a fluorescent wavelength of 510 nm was carried out. FIG. 11 shows the periodic changes in the fluorescence intensity ratio (fluorescence intensity at predetermined time/background fluorescence intensity) of the sample, where enzyme was added at 0 minutes. The RNA sample concentrations were from $10^2$ copies/30 µl to $10^5$ copies/30 µl.

A fluorescence profile depending on the initial concentration of the target RNA was obtained from FIG. 11, indicating that it is possible to measure amounts of RNA derived from the Vibrio parahaemolyticus thermostable direct hemolysin gene (tdh) present in unknown samples.

Example 11

A combination of oligonucleotide primers according to the invention was used to confirm the possibility of specific detection of tdh2-RNA as target RNA.

(1) A sample of a standard RNA (616 mer) comprising base Nos. 1 to 610 of *Vibrio parahaemolyticus* tdh2-RNA (the RNA base sequence numbering is in accordance with Nishibuchi et al. Appl. Environ. Microbiol., 58, pp.2449–2457, 1992) was quantified by ultraviolet absorption at 260 nm, and then diluted with a RNA diluent (10 mM Tris-HCl (pH 8.0), 0.1 mM EDTA, 0.5 U/µl RNase Inhibitor, 5.0 mM DDT) to $1.0 \times 10^5$ copies/5 µl. RNA (trh1-RNA and trh2-RNA) derived from the thermostable direct hemolysin-related hemolysin genes (trh1 and trh2) were also prepared as target RNA in the same manner as the tdh2-RNA. The diluent alone was used as a control test group (Nega).

(2) 20.8 µl of a reaction solution with the following composition was dispensed into a commercially available 0.5 ml volume PCR tube (GeneAmp Thin-Walled Reaction Tubes, TM of Perkin-Elmer Co., Ltd.), and 5µl of RNA sample (tdh2-RNA, trh1-RNA and trh2-RNA) was added thereto.

Composition of Reaction Solution (Final
Concentrations in Reaction System After Enzyme
Solution Addition)

60.0 mM Tris-HCl buffer (pH 8.6)

13.0 mM magnesium chloride 90.0 mM potassium chloride 1.0 mM DTT 0.25 mM each of dATP, dCTP, dGTP, dTTP 3.0 mM each of ATP, CTP, UTP 2.25 MM GTP 3.6 mM ITP 1.0 μM of first oligonucleotide primer (SEQ. ID. No.42)

1.0 μM of second oligonucleotide primer (SEQ. ID. No.48)

(The portion from the first "A" to the 28th "A" from the 5'-end in SEQ. ID. No.48 is the sequence added as the T7 polymerase promoter sequence).

0.8 μM of cleaving oligonucleotide primer (SEQ. ID. No.47; an oligonucleotide which cleaves the target RNA at the site where the second primer may bind; 3'-end thereof had been aminated)

39 U of Ribonuclease Inhibitor (Takara Shuzo Co., Ltd.)

15.0% DMSO

Distilled water for volume adjustment 25.0 nM of intercalator fluorescent dye-labeled oligonucleotide probe (TDH-YO).

39 units of Ribonuclease Inhibitor (Takara Shuzo Co., Ltd.)

15.0% DMSO

Distilled water for volume adjustment (3) The reaction solution was incubated at 41° C. for 5 minutes, and then 4.2 μl of enzyme solution pre-incubated at 41° C. for 2 minutes was added thereto.

Composition of Enzyme Solution (Final Concentrations at Time of Reaction)

1.7% sorbitol 8 units of AMV reverse transcriptase (Takara Shuzo Co., Ltd.)

142 units of T7 RNA polymerase (GIBCO Corp.)

3 μg of bovine serum albumin

Distilled water for volume adjustment (4) Next, using a temperature-controllable fluorescent spectrophotometer capable of directly measuring PCR tubes, periodic measurement of the fluorescence intensity of the reaction solution incubated at 41° C. with an excitation wavelength of 470 nm and a fluorescent wavelength of 510 nm was carried out. FIG. 12 shows the periodic changes in the fluorescence intensity ratio (fluorescence intensity at predetermined time/background fluorescence intensity) of the sample, where enzyme was added at 0 minutes. The RNA sample concentration was $10^5$ copies/30 μl.

In the systems with trh1-RNA and trh2-RNA added as the target RNA, there was an absence of fluorescence sensitivity as in the Nega group. However, specific fluorescence sensitivity was present in the system with the tdh2-RNA derived sample. This indicated that the combinations of oligonucleotides of the invention are able to specifically amplify and detect tdh-derived RNA.

Results

As explained above, the present invention provides oligonucleotide primer and oligonucleotide probe combinations which bind specifically to RNA derived from a *Vibrio parahaemolyticus* tdh even under conditions of relatively low and constant temperature (35–50° C., preferably 41° C.), which tend to cause RNA in samples to form an intramolecular structure and prevent binding of primers and probes, and they are therefore useful for rapid amplification and detection of target RNA.

Furthermore, the oligonucleotide combinations of the invention are not limited to tdh-RNA, since the complementary sequences of these oligonucleotides are useful for detection of cDNA obtained by reverse transcription of the RNA.

The base lengths of the oligonucleotides in the combinations of the invention are not limited to the listed lengths, and they also include oligonucleotides comprising at least 10 or more contiguous bases within those sequences. This is obvious from the fact that base sequences comprising about 10 bases are sufficient to ensure adequate specificity of primers or probes to target nucleic acids.

What is claimed is:

1. An isolated oligonucleotide for detection or amplification of *Vibrio parahaemolyticus* thermostable direct hemolysin-related hemolysin gene trh1 or RNA derived from said gene,
   wherein said oligonucleotide has a nucleotide sequence that comprises:
   (a) the nucleotide sequence of at least 10 contiguous bases of an oligonucleotide selected from the group consisting of SEQ ID NOS. 1, 2, 3,4, and 5, or
   (b) an oligonucleotide complementary to an oligonucleotide of said group (a); and
   wherein said isolated oligonucleotide is capable of binding specifically to a trh1 gene, or RNA derived therefrom, in the absence of heat denaturation.

2. An oligonucleotide for detection or amplification of *Vibrio parahaemolyticus* thermostable direct hemolysin-related hemolysin gene (trh1) or RNA derived from said gene, wherein said oligonucleotide has a nucleotide sequence that comprises:
   (a) the nucleotide sequence of at least 10 contiguous bases of an oligonucleotide selected from the group consisting of SEQ ID NOS. 12, 13, and 14, or
   (b) an oligonucleotide complementary to an oligonucleotide of said group (a); and
   wherein said isolated oligonucleotide is capable of binding specifically to a trh1 gene, or RNA derived therefrom, in the absence of heat denaturation.

3. The oligonucleotide of claim 1, wherein said oligonucleotide (a) is SEQ ID NO. 1, and said oligonucleotide (b) is an oligonucleotide complementary to SEQ ID NO: 1.

4. The oligonucleotide of claim 1, wherein said oligonucleotide possesses a 3' terminus that is capable of serving as a primer for amplification of said *Vibrio parahaemolyticus* thermostable direct hemolysin-related hemolysin gene (trh1), or RNA derived therefrom, in a DNA extension reaction.

5. The oligonucleotide of claim 2, wherein said oligonucleotide possesses a 3' terminus that is capable of serving as a primer for amplification of said *Vibrio parahaemolyticus* thermostable direct hemolysin-related hemolysin gene (trh1), or RNA derived therefrom, in a DNA extension reaction.

6. The oligonucleotide of claim 3, wherein said oligonucleotide possesses a 3' terminus that is capable of serving as a primer for amplification of said *Vibrio parahaemolyticus* thermostable direct hemolysin-related hemolysin gene (trh1), or RNA derived therefrom, in a DNA extension reaction.

7. The oligonucleotide of claim 1, wherein a portion of said oligonucleotide is modified or labeled with a detectable marker so as to render said oligonucleotide capable of serving as a probe for detection of *Vibrio parahaemolyticus* thermostable direct hemolysin-related hemolysin gene (trh1) or RNA derived therefrom.

8. The oligonucleotide of claim 2, wherein a portion of said oligonucleotide is modified or labeled with a detectable marker so as to render said oligonucleotide capable of serving as a probe for detection of *Vibrio parahaemolyticus* thermostable direct hemolysin-related hemolysin gene (trh1) or RNA derived therefrom.

9. The oligonucleotide of claim 3, wherein a portion of said oligonucleotide is modified or labeled with a detectable marker so as to render said oligonucleotide capable of serving as a probe for detection of *Vibrio parahaemolyticus* thermostable direct hemolysin-related hemolysin gene (trh1) or RNA derived therefrom.

* * * * *

SEQUENCE LISTING

<160> NUMBER OF SEQ ID NOS: 48

<210> SEQ ID NO 1
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 and trh2 or RNA derived therefrom

<400> SEQUENCE: 1
ttttagtttc ataattaatc                                            20

<210> SEQ ID NO 2
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 and trh2 or RNA derived therefrom

```
<400> SEQUENCE: 2
tatcgaagcc aatagcaaac                                              20

<210> SEQ ID NO 3
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 and trh2 or RNA derived therefrom

<400> SEQUENCE: 3
tccgaacctg gagaaggaaa                                              20

<210> SEQ ID NO 4
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 and trh2 or RNA derived therefrom

<400> SEQUENCE: 4
tcgttttatg tttcggtttg                                              20

<210> SEQ ID NO 5
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 and trh2 or RNA derived therefrom

<400> SEQUENCE: 5
ttaccgttat ataggcgctt                                              20

<210> SEQ ID NO 6
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 and trh2 or RNA derived therefrom

<400> SEQUENCE: 6
tagcaaactg aatgcaaagt                                              20

<210> SEQ ID NO 7
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 and trh2 or RNA derived therefrom

<400> SEQUENCE: 7
cggaaccagg agaaggaaaa                                              20

<210> SEQ ID NO 8
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 and trh2 or RNA derived therefrom

<400> SEQUENCE: 8
```
cgattgaccg tatacatctt                                                    20

<210> SEQ ID NO 9
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 and trh2 or RNA derived therefrom

<400> SEQUENCE: 9
cttggtttag gcttgttttc                                                    20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 and trh2 or RNA derived therefrom

<400> SEQUENCE: 10
ggtattgatt cttcgctatc                                                    20

<210> SEQ ID NO 11
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 and trh2 or RNA derived therefrom

<400> SEQUENCE: 11
ataacaaaca tatgtccatt                                                    20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 or RNA derived therefrom

<400> SEQUENCE: 12
tgaagtcgtg aaaatagatt                                                    20

<210> SEQ ID NO 13
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 or RNA derived therefrom

<400> SEQUENCE: 13
gaatagttct gatttaggct                                                    20

<210> SEQ ID NO 14
<211> LENGTH: 20
<212> TYPE: DNA
<213> ORGANISM: Artificial Sequence
<220> FEATURE:
<223> OTHER INFORMATION: oligonucleotide capable of binding specifically
      to trh1 or RNA derived therefrom

<400> SEQUENCE: 14

```
atgatgattt attggaaata                                              20

<210> SEQ ID NO 15
<211> LENGTH: 20
<212> TYPE: DNA
<213> ORGANIZATION: Artificial Sequence
<220> FEATURE:
<223> OTHER INFORMATION: oligonucleotide capable of binding specifically
      to trh2 or RNA derived therefrom

<400> SEQUENCE: 15
gatttagata ttgaaaatat                                              20

<210> SEQ ID NO 16
<211> LENGTH: 20
<212> TYPE: DNA
<213> ORGANISM: Artificial Sequence
<220> FEATURE:
<223> OTHER INFORMATION: oligonucleotide capable of binding specifically
      to trh2 or RNA derived therefrom

<400> SEQUENCE: 16
gtgaccattg atgttgactg                                              20

<210> SEQ ID NO 17
<211> LENGTH: 20
<212> TYPE: DNA
<213> ORGANISM: Artificial Sequence
<220> FEATURE:
<223> OTHER INFORMATION: oligonucleotide capable of binding specifically
      to trh2 or RNA derived therefrom

<400> SEQUENCE: 17
ttgtgaagac cgtagaagta                                              20

<210> SEQ ID NO 18
<211> LENGTH: 20
<212> TYPE: DNA
<213> ORGANISM: Artificial Sequence
<220> FEATURE:
<223> OTHER INFORMATION: oligonucleotide capable of binding specifically
      to tdh2 or RNA derived therefrom

<400> SEQUENCE: 18
atggatataa ataaaaatga                                              20

<210> SEQ ID NO 19
<211> LENGTH: 20
<212> TYPE: DNA
<213> ORGANISM: Artificial Sequence
<220> FEATURE:
<223> OTHER INFORMATION: oligonucleotide capable of binding specifically
      to tdh2 or RNA derived therefrom

<400> SEQUENCE: 19
gttgtatctc gaacaacaaa                                              20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide capable of binding specifically
      to tdh2 or RNA derived therefrom

<400> SEQUENCE: 20
tttgtacggt tttctttta                                               20
```

<210> SEQ ID NO 21
<211> LENGTH: 20
<212> TYPE: DNA
<213> ORGANISM: Artificial Sequence
<220> FEATURE:
<223> OTHER INFORMATION: oligonucleotide capable of binding specifically to tdh2 or RNA derived therefrom

<400> SEQUENCE: 21
ctgacgttgt gaatactgat                                                    20

<210> SEQ ID NO 22
<211> LENGTH: 20
<212> TYPE: DNA
<213> ORGANISM: Artificial Sequence
<220> FEATURE:
<223> OTHER INFORMATION: oligonucleotide capable of binding specifically to tdh2 or RNA derived therefrom

<400> SEQUENCE: 22
agctgtactt gatctgattt                                                    20

<210> SEQ ID NO 23
<211> LENGTH: 20
<212> TYPE: DNA
<213> ORGANISM: Artificial Sequence
<220> FEATURE:
<223> OTHER INFORMATION: oligonucleotide capable of binding specifically to tdh2 or RNA derived therefrom

<400> SEQUENCE: 23
atagaatctt catcttcacc                                                    20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide capable of binding specifically to tdh2 or RNA derived therefrom

<400> SEQUENCE: 24
attaccaata tattaccact                                                    20

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
atgatgattt attggaaata c                                                  21

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
agaactattc ttctgttagt gatttcgttg                                         30

<210> SEQ ID NO 27

```
<211> LENGTH: 20
<212> TYPE: DNA
<213> ORGANISM: Artificial Sequence
<220> FEATURE:
<223> OTHER INFORMATION: primer

<400> SEQUENCE: 27
gaatagttct gatttaggct                                              20

<210> SEQ ID NO 28
<211> LENGTH: 51
<212> TYPE: DNA
<213> ORGANISM: Artificial Sequence
<220> FEATURE:
<223> OTHER INFORMATION: primer

<400> SEQUENCE: 28
aattctaata cgactcacta tagggagaag aactattctt ctgttagtga t           51

<210> SEQ ID NO 29
<211> LENGTH: 53
<212> TYPE: DNA
<213> ORGANISM: Artificial Sequence
<220> FEATURE:
<223> OTHER INFORMATION: primer

<400> SEQUENCE: 29
aattctaata cgactcacta tagggagata ttcttctgtt agtgatttcg ttg         53

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
ggcaatgatt cttcattttc                                              20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
tcgacattga cgaaatattc                                              20

<210> SEQ ID NO 32
<211> LENGTH: 19
<212> TYPE: DNA
<213> ORGANISM: Artificial Sequence
<220> FEATURE:
<223> OTHER INFORMATION: primer

<400> SEQUENCE: 32
cacataacaa acatatgcc                                               19

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
```
gtgaccattg atgttgactg                                            20

<210> SEQ ID NO 34
<211> LENGTH: 29
<212> TYPE: DNA
<213> ORGANISM: Artificial Sequence
<220> FEATURE:
<223> OTHER INFORMATION: primer

<400> SEQUENCE: 34
tatctaaatc attcgcgatt gatctgcca                                  29

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
gatttagata ttgaaaatat                                            20

<210> SEQ ID NO 36
<211> LENGTH: 49
<212> TYPE: DNA
<213> ORGANISM: Artificial Sequence
<220> FEATURE:
<223> OTHER INFORMATION: primer

<400> SEQUENCE: 36
aattctaata cgactcacta tagggagata tctaaatcat tcgcgattg            49

<210> SEQ ID NO 37
<211> LENGTH: 52
<212> TYPE: DNA
<213> ORGANISM: Artificial Sequence
<220> FEATURE:
<223> OTHER INFORMATION: primer

<400> SEQUENCE: 37
aattctaata cgactcacta tagggagaaa atcattcgcg attgatctgc ca        52

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
cgattgaccg tatacatctt                                            20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
agctgtactt gatctgattt                                            20

<210> SEQ ID NO 40
<211> LENGTH: 28
<212> TYPE: DNA

```
<213> ORGANISM: Artificial Sequence
<220> FEATURE:
<223> OTHER INFORMATION: primer

<400> SEQUENCE: 40
ttatatccat gttggctgca ttcaaaac                              28

<210> SEQ ID NO 41
<211> LENGTH: 28
<212> TYPE: DNA
<213> ORGANISM: Artificial Sequence
<220> FEATURE:
<223> OTHER INFORMATION: primer

<400> SEQUENCE: 41
gagatacaac ttttaatacc aatgcacc                              28

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
attaccaata tattaccact                                       20

<210> SEQ ID NO 43
<211> LENGTH: 51
<212> TYPE: DNA
<213> ORGANISM: Artificial Sequence
<220> FEATURE:
<223> OTHER INFORMATION: primer

<400> SEQUENCE: 43
aattctaata cgactcacta tagggagatt atatccatgt tggctgcatt c    51

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
atggatataa ataaaaatga                                       20

<210> SEQ ID NO 45
<211> LENGTH: 51
<212> TYPE: DNA
<213> ORGANISM: Artificial Sequence
<220> FEATURE:
<223> OTHER INFORMATION: primer

<400> SEQUENCE: 45
aattctaata cgactcacta tagggagatc catgttggct gcattcaaaa c    51

<210> SEQ ID NO 46
<211> LENGTH: 52
<212> TYPE: DNA
<213> ORGANISM: Artificial Sequence
<220> FEATURE:
<223> OTHER INFORMATION: primer

<400> SEQUENCE: 46
aattctaata cgactcacta tagggagaga gatacaactt ttaataccaa tg   52
```

```
<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
gttgtatctc gaacaacaaa                                              20

<210> SEQ ID NO 48
<211> LENGTH: 51
<212> TYPE: DNA
<213> ORGANISM: Artificial Sequence
<220> FEATURE:
<223> OTHER INFORMATION: primer

<400> SEQUENCE: 48
aattctaata cgactcacta tagggagaac aacttttaat accaatgcac c           51
```